US008354438B2

(12) United States Patent
Chez

(10) Patent No.: US 8,354,438 B2
(45) Date of Patent: Jan. 15, 2013

(54) NEUROLOGICAL FUNCTIONS

(76) Inventor: Michael Chez, Granite Bay, CA (US)

(*) Notice: Subject to any disclaimer, the term of this patent is extended or adjusted under 35 U.S.C. 154(b) by 1796 days.

(21) Appl. No.: 10/486,077

(22) PCT Filed: Jul. 15, 2002

(86) PCT No.: PCT/US02/22341
§ 371 (c)(1),
(2), (4) Date: Feb. 10, 2005

(87) PCT Pub. No.: WO03/013514
PCT Pub. Date: Feb. 20, 2003

(65) Prior Publication Data
US 2006/0052428 A1    Mar. 9, 2006

Related U.S. Application Data

(60) Provisional application No. 60/325,136, filed on Sep. 27, 2001, provisional application No. 60/310,710, filed on Aug. 8, 2001.

(51) Int. Cl.
*A61K 31/425* (2006.01)
(52) U.S. Cl. ...................... 514/365; 514/370
(58) Field of Classification Search .......... 514/365, 514/367
See application file for complete search history.

(56) References Cited

U.S. PATENT DOCUMENTS

| 4,981,846 | A | 1/1991 | Matsukura et al. |
| 4,994,467 | A * | 2/1991 | Zimmerman ................ 514/284 |
| 6,054,482 | A * | 4/2000 | Augart et al. ................ 514/561 |
| 7,456,224 | B2 | 11/2008 | Chez |
| 7,709,213 | B2 | 5/2010 | Chez |
| 2006/0079495 | A1 | 4/2006 | Blum |
| 2006/0188505 | A1 | 8/2006 | Skurkovich et al. |
| 2008/0108643 | A1 | 5/2008 | Chez |
| 2008/0269123 | A1 | 10/2008 | Li et al. |
| 2009/0048348 | A1 | 2/2009 | Chez |

FOREIGN PATENT DOCUMENTS

JP          9020661 A    1/1997

OTHER PUBLICATIONS

Cohen Met Al: "Serum Carnosinase Deficiency a Non-Disabling Phenotype" & Journal of Mental Deficiency Research, vol. 29, No. 4, 1985, pp. 383-390,.*
Boldyrev et al., Neuroscience, 1999;94(2):571-577.*
Isaacson et al., Journal of Applied Nutrition, 1996, 48(4):110-118.*
Stvolinsky et al., Biochemistry, 2000;65(7):849-855.*
Chez, MD, Michael G., et al. "Double-Blind, Placebo-Controlled Study of L-Carnosine Supplementation in Children with Autistic Spectrum Disorders", Journal of Child Neurology, 2002, vol. 17, No. 11, 833-37.
De Marchis, et al., "Carnosine-Related, Dipeptides in Neurons and Glia," Biochemistry, 2000, pp. 824-833,vol. 65, No. 7.

Stvolinsky S. L., et al., "Anti-ischemic Activity of Carnosine," Biochemistry, 2000, pp. 849-855, vol. 65, No. 7.
Abstract of Quinn, Peter J., et al., "Carnosine: Its Properties, Functions and Potential Therapeutic Applications," Molecular Aspects of Medicine, 1992, pp. 379-444, vol. 13, issue 5.
Abstract of Kish, Stephen J, et al., "Regional Distribution of Homocarnosine, Homocarnosine-Carnosine Synthetase and Homocarnosinase in Human Brain," Journal of Neurochemistry, Jun. 1979, pp. 1629-1636, vol. 32, issue 6.
Abstract of Trombley, PQ, et al., "Interactions Between Carnosine and Zinc and Copper: Implications for Neuromodulation and Neuroprotections," Biochemistry, Jul. 2000, pp. 807-816, vol. 65, No. 7.
Hipkiss, A. R., "Carnosine and Protein Carbonyl Groups: A Possible Relationship," Biochemistry, 2000, pp. 771-778, vol. 65, No. 7.
Wang, A. M., et al., "Use of Carnosine as a Natural Anti-senescence Drug for Human Beings," Biochemistry, Nov. 7, 2000, pp. 869-871, vol. 65, No. 7.
Gallant, S., "Carnosine as a Potential Anti-senescence Drug," Biochemistry, 2000, pp. 866-868, vol. 65, No. 7.
Matsukura, T., "Applicability of Zinc Complex of L-Carnosine for Medical Use," Biochemistry, Nov. 7, 2000, pp. 817-823, vol. 65, No. 7.
Abstract of Stvolinksy, Serguei, L., et al., "Carnosine: An Endogenous Neuroprotector in the Ischemic Brain, Cellular and Molecular Neurobiology", 1999, pp. 45-56, vol. 19, No. 1.
Abe, H. "Role of Histidine-Related Compounds as Intracellular Proton Buffering Constituents in Vertebrate Muscle," Biochemistry, 2000, pp. 757-765, vol. 65, No. 7.
Holliday, R., et al. "A Role for Carnosine in Cellular Maintenance," Biochemistry, 2000, pp. 991-997, vol. 65, No. 7.
Stuerenburg, H. J., et al., "The Roles of Carosine in Aging of Skeletal Muscle and in Neuromuscular Diseases," Biochemistry, 2000, pp. 862-865, vol. 65, No. 7.
Abstract of Hipkiss, A. R., et al., "A Possible New Role for the Anti-Ageing Peptide Carosine," Cellular and Molecular Life Science, May 2000, pp. 747-753, vol. 57, No. 5.
Abstract of Boldyrev et al., "Metabolic Transformation of Neuropeptide Carnosine Modifies its Biological Activity," Cellular and Molecular Nerobiology, 1999, pp. 163-175, vol. 19, No. 1.
Baran, E. J., "Metal Complexes of Carnosine," Biochemistry, 2000, pp. 789-797, vol. 65, No. 7.
Chez, Michael G., et al., "Frequency of Epileptiform EEG Abnormalities in a Sequential Screening of Autistic Patients with No Known Clinical Epilepsy from 1996 to 2005," Epilepsy & Behavior, 2006, pp. 267-271, vol. 8, issue 1.
Abstract of Fontana, M., et al., "Prevention of Peroxynitrite-Dependent Damage by Carnosine and Related Sulphonamido Pseudodipeptides," Cellular and Molecular Life Science, Mar. 2002, pp. 546-551, vol. 59, No. 3.
Abstract of Bradford, H. F., "Glutamate, GABA and Epilepsy," Progress in Neurobiology, Dec. 1995, pp. 477-511, vol. 47, issue 6.
Abstract of Yoshikawa, T., et al., "Effect of Zinc-Carnosine Chelate Compound (Z-103), A Novel Antioxidant, on Acute Gastric Mucosal Injury Induced by Ischemia-Reperfusion in Rats," Free Radical Res, 1991, pp. 289-296, vol. 14, No. 4.
Abstract of Petroff, OA, et al., "Homocarnosine and Seizure Control in Juvenile Myoclonic Epilepsy and Complex Partial Seizures," Neurology, Mar. 2001, pp. 709-715, vol. 56, No. 6.

(Continued)

*Primary Examiner* — San-Ming Hui
(74) *Attorney, Agent, or Firm* — Cahn & Samuels, LLP

(57) ABSTRACT

The present invention relates to materials and methods for treating neurological diseases and disorders including but not limited to epilepsy and autism, as well as general cognitive problems.

10 Claims, No Drawings

OTHER PUBLICATIONS

Abstract of Horning, et al., "Endogenous Mechanisms of Neuroprotection: Role of Zinc, Copper, and Carnosine," Brian Research, Jan. 3, 2000, pp. 56-61, vol. 852, issue 1.

Abstract of Peltola et al., "Autoantibodies to glutamic acid decarboxylase in patients with therapy-resistant epilepsy," Neurology 2000, 55: 46-50.

Abstract of Meldrum, "Epilepsy and γ-aminobutyric acid-mediated inhibition", Int. Rev. Neurobiol. 17:1-36, 1975.

Abstract of Kohen et al., "The SOD like activity of copper:carnosine, copper:anserine and copper: homocarnosine complexes," Free Radic Res Commun, 1991:12-13 1:179-85.

Abstract of Takahashi. "Studies on homocarnosine in cerebrospinal fluid in infancy and childhood. Part II. Homocarnosine levels in cerebrospinal fluid from children with epilepsy, febrile convulsion or meningitis," Brain Dev., 1981 3(3):263-70.

Bakardjiev, et al., "Biosynthesis, Release, and Uptake of Carnosine in Primary Cultures," Biochemistry, 2000, pp. 779-782, vol. 65, No. 7.

Chez, M., et al., "Practical Treatment with Pulse Does Corticosteroids in Pervasive Developmental Delay or Autistic Patients with Abnormal Paitents with Abnormal Epileptiform Sleep EEG and Language Delay," 8th International Child Neurology Congress, Sep. 1998, pp. 695-698.

Connolly A., et al., "Serum autoantibodies to brain in Landau-Kleffner Variant, Autism, and other Neurologic Disorders," J. Pediatr., 1999, pp. 607-613.

Chez, M., et al., "Relationship of Epileptic Activity in Autism and Pervasive Developmental Disorder to Possible Autoimmune Encephalopathy," The Journal of Developmental and Learning Disorders, 1999, pp. 118-125, issue 2.

Abstract of Belsito, KM, et al. "Lamotrigine Therapy for Autistic Disorder: A Randomized, Double-Blind, Placebo-Controlled Trial," J Autism Dev. Disord. Apr. 2001, pp. 175-181, vol. 31, No. 2.

Chez, MD, Michael G., et al. "Double-Blind, Placebo-Controlled Study of L-Carnosine Supplementation in Children with Autistic Spectrum Disorder", Journal of Mental Deficiency Research, 1985, pp. 383-390, vol. 29, No. 4.

Kang Kyung-Sun, et al., "Protective Effect of L-Carnosine Against 12-0-tetradecanoylphorbol-13-acetate- or Hydrogen Peroxide-Induced Apoptosis on V-myc Transformed Rat Liver Epithelial Cells", Cancer Letters, Apr. 8, 2008, pp. 53-62, vol. 178, No. 1.

Smythies, J., "The Neurochemical Basis of Learning and Neurocomputation: The Redox Theory", Behavioural Brian Research, Feb. 15, 1999, pp. 1-6, vol. 99, No. 1.

Stvolinsky, Serguei, L, et al., "Carnosine: An Endogenous Neuroprotector in the Ischemic Brain", Cellular and Molecular Neurobiology, Feb. 1999, pp. 45-56, vol. 19, No. 1.

English Abstract of JP 09 20661 A.

Cohen, M., et al., "Serum Carnosinase Deficiency a Non-Disabling Phenotype", Journal of Mental Deficiency Research, 1985, pp. 383-390, vol. 29, No. 4.

International Search Report received at International Bureau on Nov. 6, 2002.

* cited by examiner

NEUROLOGICAL FUNCTIONS

This application is a U.S. national stage application of PCT/US02/22341 filed on Jul. 15, 2002 and claims priority benefit of U.S. Provisional Application No. 60/325,136, filed Sep. 27, 2001, and U.S. Provisional Application No. 60/310,710, filed Aug. 8, 2001, both incorporated herein by reference in their entirety.

FIELD OF INVENTION

The present invention relates to materials and methods for treating neurological diseases and disorders including but not limited to epilepsy and autism, as well as general cognitive problems.

BACKGROUND

Many neurological disorders are presently incurable, but are treatable with medications that alleviate symptoms and/or improve cognitive function. One of the principal neurological disorders, independent of age, is epilepsy. Over 10% of the population will experience at least one seizure. However, the prevalence of epilepsy does vary with age, and is high during infancy, diminishes during childhood; reaches a nadir during both adolescence and adulthood, and then goes up significantly in old age. Epileptics are characterized by the incidence of seizures, although seizures also occur in other neurological disorders, and even in the absence of a disorder. Seizures are induced by transient, paroxysmal, and synchronous neuronal discharges. How a seizure manifests itself will depend on the locus and quantity of neurons involved, as well as how long a seizure discharge lasts. Willmore, J. and Wheless, J. Scientific American Medicine, sect. 11, chp 12, www.samed.com.

In contrast to the isolated seizure, epilepsy may be defined as reoccurring seizures and may be genetic or environmental in origin. Based on clinical and electroencephalographic criteria, the International League Against Epilepsy developed a widely accepted classification scheme for epilepsy, which divides seizures into three major categories: partial, generalized, and unclassified. In addition to the epilepsy classification, there is also a classification of "epilepsy syndromes": benign childhood epilepsy with centrotemporal spikes, childhood absence epilepsy, juvenile myoclonic epilepsy, chronic progressive epilepsia partialis continua, and severe myoclonic epilepsy of childhood.

Drug therapy is the most common seizure treatment. Although antiseizure medications, known as antiepileptic drugs (AED) or anticonvulsants, had been available earlier, the introduction of phenobarbital in the early twentieth century issued in the modern era of AEDs. Willmore, J. and Wheless, J. Scientific American Medicine, sect. 11, chp 12, www.samed.com. While most AEDs were introduced before 1980, several new drugs have been recently licensed for use in epilepsy, and additional drugs in the pipeline are destined for approval in the coming years. Nevertheless there is a continuing need for new AEDs and epileptic therapies since existing therapies are not always effective or effective as they need to be.

Epileptic seizures can occur in a wide variety of disorders including the autistic spectrum disorders, also known as pervasive developmental disorders. Autistic spectrum disorders (ASD), including, but not limited to Autistic Disorder (autism), pervasive developmental delay not otherwise specified, Rhett's disorder, childhood disintegrative disorder, and Asperger's syndrome (see *American Psychiatric Association, Diagnostic and Statistical Manual of Mental Disorders*, 4th ed., American Psychiatric Association, Washington, 1993, pp. 65-78), are long term, developmental disorders with no known or agreed upon nervous system pathology or definitive genetic site. Rodier, P. M, J. et al., *Comparative Neurology* 1996; 370:247-261; Bachevalier, J., *Neuropsychology* 1994; 32:627-648. Unfortunately, very few double-blind studies have been performed involving ASD, due to the different degrees of presentation and the multiple phenotypes of the disease. The varying symptoms observed within the ASD syndrome indicate more than a single region of injury that results in an assortment of behaviors. Rodier, P. M, J. et al., *Comparative Neurology* 1996; 370:247-261. With no available cure, existing treatments are directed to modifying the course of the disease.

Pervasive developmental disorders are characterized by severe and pervasive impairment in several areas of development, reciprocal social interaction skills, communication skills, or the presence of stereotyped behavior, interests and activities. *American Psychiatric Association, Diagnostic and Statistical Manual of Mental Disorders*, 4th ed., American Psychiatric Association, Washington, 1993, pp. 65-78. The principal criteria of autism include significantly abnormal or impaired development in social interaction and communication and a significantly restricted repertoire of activity and interests. *American Psychiatric Association, Diagnostic and Statistical Manual of Mental Disorders*, 4th ed., American Psychiatric Association, Washington, 1993, pp. 65-78. Depending on the developmental level and chronological age of the individual, how the disorder manifests itself can be very different.

Autism or autistic disorder is the most well known of the spectrum disorders, and is also known as early infantile autism, childhood autism and Kanner's autism. *American Psychiatric Association, Diagnostic and Statistical Manual of Mental Disorders*, 4th ed., American Psychiatric Association, Washington, 1993, pp. 65-78. Research in the past several years has shown an association between sleep electroencephalograms (EEGs) and autism. Tuchman, R., et al. *CNS Spectrums* 1998; 3:61-X; Deykin, E. Y. and MacMahon, B., *Am. J. Psychiatry* 1979; 136:1310-1312; Lewine, J. D. et al. *Pediatrics* 1999; 104:405-418; Tuchman, R. F. and Rapin, I. *Pediatrics* 1997; 99:560-566; Tuchman, R. F. et al., *Pediatrics* 1991; 88:1219-1225.

One-third of autistic children suffer one or more seizures by adolescence, perhaps linking epileptiform activity with some instances of ASD. Lewine, J. D. et al. *Pediatrics* 1999; 104:405-418. Magnetoencephalographic data has suggested that the percentage may even be higher; in a recent autistic study, 14% more children were identified as having epileptiform activity by MEG (82%) that were not identified by concurrent EEGs (68%). For more on diagnosis and testing of autism, see Barthelemy, C. et al., *Brain Dysfunct.* 3:271-84 (1990); *American Psychiatric Association, Diagnostic and Statistical Manual of Mental Disorders*, 4th ed., American Psychiatric Association, Washington, 1993, pp. 65-78., and Gillberg, C., *Brain Dysfunct* 3:249-60 (1990).

An approach that treats the symptoms and potentially the causes of autism is the individualized nutrient therapy for autism, such as that reported in Isaacson et al., Journal of Applied Nutrition, 48, 110-118 (1996), the Autism Research Publication "Patient Ratings of Behavioral Effects of Drugs, Nutrients, and Diets", ARI Publ. 34, Autism Research Institute, 4182 Adams Avenue, San Diego, Calif. 92116, September 2000, as well as in other references. This individualized therapy relies on treatment optimized for the individual's particular chemical imbalance, with particular nutrients emphasized in certain imbalances, and others avoided. Such individualized therapy is expensive, and a need exists for effective, cost-effective therapies for autism.

Attention Deficit and Disruptive Behavior Disorders constitute another, but related set of neurological disorders. Attention Deficit Disorder (ADD) also known as Attention Deficit Hyperactive Disorder (ADHD) is characterized by a persistent pattern of inattention and/or hyperactivity-impulsivity that is both more frequent and more severe than what is typically observed in individuals of a comparable developmental stage. *American Psychiatric Association, Diagnostic and Statistical Manual of Mental Disorders*, 4th ed., American Psychiatric Association, Washington, 1993, pp. 65-78. The inattention may be manifest in academic, occupational, or social situations. *American Psychiatric Association, Diagnostic and Statistical Manual of Mental Disorders*, 4th ed., American Psychiatric Association, Washington, 1993, pp. 65-78.

Improved treatments are also needed for Cerebral palsy (CP). CP syndromes are a group of related motor disorders originating usually from either developmental abnormalities or perinatal or postnatal central nervous system (CNS) disorder damage occurring before 5 years of age. CP is characterized by impaired voluntary movement. While the term CP is not itself a diagnosis, the term does provide a useful classification of individuals who may suffer from nonprogressive spasticity, ataxia, or involuntary movements. Approximately a quarter of individuals with CP experience convulsive seizures. *The Merck Manual*, Merck Research Laboratories, 16th ed. 1992.

Improved treatments are also needed for Tourette's (Gilles de la Tourette's) Syndrome. Tourette's Syndrome comprises both multiple motor and one or more vocal tics, occurring over a period of at least one year, at least intermittently, but sometimes as frequently as many times daily. Obsessions, compulsions, hyperactivity, distractability, and impulsivity are often associated. Onset is in childhood, and tics often lessen in severity and frequency and may even remit during adolescence and adulthood. *Dorland's Illustrated Medical Dictionary*, 29th ed., W.B. Saunders Co., 2000.

Improved treatments are also needed for apraxias. Apraxias are defined by the inability to execute purposeful learned motor acts, even though the patient has the physical ability and willingness to perform the relevant act. Apraxias are commonly found in many metabolic and structural diseases that involve the brain diffusely, particularly those that seem to impair frontal lobe function. In a typical case, a patient cannot follow a motor command even though he or she understand it and can perform individual components of the command. The defect appears to be caused by a lesion in the neural pathways that retain memories of learned movement patterns, resulting in an inability to conceptualize necessary patterns in order to perform actions. *The Merck Manual*, Merck Research Laboratories, 16th ed. 1992. Specific apraxias include, but are not limited to, motor and speech apraxias. Motor or innervatory apraxia are characterized by impairment of skilled movements that is greater than different in form from that caused by weakness of the affected parts with the patient appearing clumsy rather than weak. *Dorland's Illustrated Medical Dictionary*, 29th ed., W.B. Saunders Co., 2000. Speech apraxia is caused by apraxia of mouth and neck muscles due to a lesion interfering with coordination of impulses from Broca's region. *Dorland's Illustrated Medical Dictionary*, 29th ed, W.B. Saunders Co., 2000.

Improved treatments are also needed for central auditory processing disorders. Central auditory processing disorders are characterized by hearing difficulties due to fundamental deficiencies in cognitive processing as well as to deficits in auditory perceptual processes. http://www.lindamoodbell.com/definitions/centralauditory.htm Improved treatments are also needed for bipolar disorder (bipolar mood disorder). Bipolar disorder usually begins with depression, and includes at least one period of elation. *The Merck Manual*, Merck Research Laboratories, 16th ed. 1992.

Improved treatments are also needed for panic disorders (anxiety neurosis, generalized anxiety disorder and anxiety reaction). Panic disorders are characterized by chronic, unrealistic anxiety often punctuated by acute attacks of anxiety or panic. Attacks associated with panic disorders can occur repeatedly over a period of time, with durations of anywhere between a few minutes to an hour or two. *The Merck Manual*, Merck Research Laboratories, 16th ed. 1992.

Improved treatments are also needed for dyslexia. While there is no universally accepted definition or set of diagnostic criteria for dyslexia, the condition can be defined generally as a condition that interferes with learning to read even though an individual has average or above-average intelligence, adequate motivation and educational opportunities, socioeconomic advantage, and normal sensory acuity. *The Merck Manual*, Merck Research Laboratories, 16th ed. 1992.

Improved treatments are also needed for Down's Syndrome. Down's syndrome is a trisomy resulting from an extra full or partial copy of chromosome twenty-one. Diagnosis and characterization of Down's syndrome is well known in the art.

The aforementioned conditions remain some of the least understood and difficult to treat diseases and disorders, especially amongst those conditions that afflict children. There has been a long felt need for improved therapies for all of these neurological conditions.

SUMMARY OF INVENTION

The present invention addresses one or more needs in neurology by providing materials and methods for the treatment of human disorders, such as autism, epilepsy, seizures, pervasive developmental disorder, cerebral palsy, Tourette's Syndrome, attention deficit disorder, attention deficit hyperactive disorder, central auditory processing disorder, dyslexia, apraxia of speech, motor type apraxia, panic disorder, bipolar disorder, Down's Syndrome and Asperger's Syndrome. The materials and methods generally involve compositions comprising a compound of the following formula:

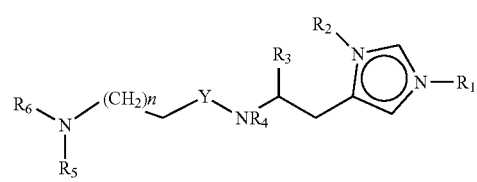

wherein Y is C=O (carbonyl), or $SO_2$, (sulphonyl); $R_1$ is H (hydrogen) or $CH_3$ (methyl), with the qualification that $R_1$ is null when $R_2$ is substituted; $R_2$ is H or $CH_3$, with the qualification that $R_2$ is null when $R_1$ is substituted; $R_3$ is COOH (carboxyl) or H; $R_4$ is H; $R_5$ is H or $COCH_3$ (acetyl), with the qualification that $R_5$ is H when $R_6$ is $COCH_3$; $R_6$ is H or $COCH_3$, with the qualification that $R_6$ is H when $R_5$ is $COCH_3$; and wherein n is 1 or 2; as well as pharmaceutically acceptable salts, hydrates, or prodrugs of these compounds.

Of these compounds, carnosine and its pharmaceutically acceptable salts, hydrates, or prodrug formulations is highly preferred.

Thus, in one embodiment, the invention comprises a method of improving neurological function in a human subject comprising identifying a human subject having one or more of the foregoing neurological conditions, and administering to the subject a composition comprising one or more of the compounds represented by the above formula.

In a related aspect, the invention comprises use of compounds represented by the above formula in the manufacture of a medicament for treating any of the aforementioned diseases.

Many of the neurological conditions identified above are currently treated with a variety of pharmaceutical agents. In another variation, the invention comprises materials and methods for improving such agents, and such therapy, for the various neurological conditions.

Thus, for example, for any treatment methodology for any of the foregoing conditions that involves administering a particular medicine or medicines to a human subject, the invention provides an improved method that additionally comprises administering a composition comprising one or more of the above-described compounds. In one variation, the medicine and the composition are administered separately. In another variation, they are administered concurrently. In yet another variation, they are administered as a single composition containing both the compound and the medicine. Irrespective of the variation, it is contemplated that administration of such compounds will increase the efficacy of the medicine.

In a related aspect, the invention comprises use of compounds of the formula provided above in the manufacture of a medicament for the treatment of any of the disorders identified above, where the medicament further includes other accepted medicines for the treatment of the disorder.

Similarly, the invention provides methods of formulating the active ingredients of any medicines for treatment of the foregoing disorders, the method comprising including in the formulation one or more compounds having the structure set forth above.

Likewise, the invention provides a composition comprising a neuromodulator, selected from the group consisting of anticonvulsant medication, selective serotonin reuptake inhibitor medication, acetylcholinesterase medication, pervasive developmental disorder medication, attention deficit disorder/attention deficit hyperactive disorder (ADD/ADHD) medication, and stimulant medication, in admixture with a compound of the formula set forth above.

For any composition or formulation of the invention, it is contemplated that additional materials would be included, such as pharmaceutically acceptable diluents, adjuvants, excipients, or carriers.

In still another related variation, the invention comprises a unit dose comprising: a first compound selected from the group consisting of anticonvulsant medication, selective serotonin reuptake inhibitor medication, acetylcholinesterase medication, pervasive developmental disorder medication, attention deficit disorder/attention deficit hyperactive disorder (ADD/ADHD) medication, and stimulant medication; and a second compound of the formula set forth above. Unit doses of the invention would embrace compositions of the invention, and would also embrace situations where the medicine and the compound are packaged together for co-administration, but are not in admixture. The inclusion of a label with directions (treatment instructions) for usage of both agents in a combined therapy is indicative of a unit dose of the invention.

Similarly, the invention includes kits which comprise compounds or compositions packaged together in a manner which facilitates their use to practice methods of the invention. In a simplest embodiment, such a kit includes a composition comprising a compound of the formula set forth above, packaged in a container such as a sealed bottle or vessel, with a label affixed to the container or included in the package that describes use of the compound or composition to practice a method of the invention. Preferably, the compound or composition is packaged in a unit dosage form.

Additional features and variations of the invention will be apparent to those skilled in the art from the entirety of this application, especially the detailed description which follows, and all such features are intended as aspects of the invention.

Likewise, features of the invention described herein can be recombined into additional embodiments that also are intended as aspects of the invention, irrespective of whether the combination of features is specifically mentioned above as an aspect or embodiment of the invention. Also, only such limitations which are described herein as critical to the invention should be viewed as such; variations of the invention lacking limitations which have not been described herein as critical are intended as aspects of the invention.

Aspects of the invention described by groupings (genera) of compounds, compositions, diseases, conditions, and so on, or numberical ranges are described that way for conciseness. Individual members of groups are each individually contemplated as separate aspects of the invention, and all permutations of subgroups are contemplated as aspects of the invention.

In addition to the foregoing, the invention includes, as an additional aspect, all embodiments of the invention narrower in scope in any way than the variations specifically mentioned above. Although the applicant(s) invented the full scope of the claims appended hereto, the claims appended hereto are not intended to encompass within their scope the prior art work of others. Therefore, in the event that statutory prior art within the scope of a claim is brought to the attention of the applicants by a Patent Office or other entity or individual, the applicant(s) reserve the right to exercise amendment rights under applicable patent laws to redefine the subject matter of such a claim to specifically exclude such statutory prior art or obvious variations of statutory prior art from the scope of such a claim. Variations of the invention defined by such amended claims also are intended as aspects of the invention.

DETAILED DESCRIPTION OF THE INVENTION

As summarized above, the present invention provides materials and methods which generally involve compositions comprising a compound of the following formula (hereinafter Formula I):

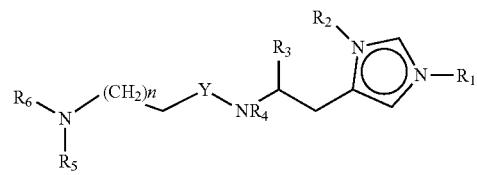

wherein Y is C=O (carbonyl), or $SO_2$, (sulphonyl); $R_1$ is H or $CH_3$, with the qualification that $R_1$ is null when $R_2$ is substituted; $R_2$ is H or $CH_3$, with the qualification that $R_2$ is null when $R_1$ is substituted; $R_3$ is COOH (carboxyl) or H; $R_4$ is H; $R_5$ is H or $COCH_3$, with the qualification that $R_5$ is H when $R_6$ is $COCH_3$; $R_6$ is H or $COCH_3$, with the qualification that $R_6$ is H when $R_5$ is $COCH_3$; and wherein n is 1 or 2; as well as pharmaceutically acceptable salts, hydrates, or prodrugs of these compounds.

When n=1 and either $R_1$ or $R_2$ is H (hydrogen), $R_3$ is a carboxyl group (COOH), $R_4$ is a hydrogen, Y is a carbonyl group (C=O), and both $R_5$ and $R_6$ are H, then the compound described is carnosine. When n=2 and either $R_1$ or $R_2$ is H (hydrogen), R3 is a carboxyl group (COOH), $R_4$ is a hydrogen, Y is a carbonyl group (C=O), and both $R_5$ and $R_6$ are H, then the compound described is homocarnosine. When n=1, and $R_1$ is a $CH_3$(methyl), $R_2$ is a H (hydrogen), R3 is a carboxyl group (COOH), $R_4$ is a hydrogen, Y is a carbonyl group (C=O), and both $R_5$ and $R_6$ are H, then the compound described is anserine. When n=1 and $R_1$ is a H(Hydrogen), $R_2$ is $CH_3$ (methyl), R3 is a carboxyl group (COOH), $R_4$ is a hydrogen, Y is a carbonyl group (C=O), and both $R_5$ and $R_6$ are H, then the compound described is ophidine (ofidine). When $R_5$ or $R_6$ is an acetyl group ($COCH_3$), then the compound is an acetylated Formula I compound. When n=1 and either $R_1$ or $R_2$ is H (hydrogen), R3 is a hydrogen, $R_4$ is a hydrogen, Y is a carbonyl group (C=O), and both $R_5$ and $R_6$ are H, then the compound described is carnicine. When Y is a sulphonyl ($SO_2$), as opposed to a carbonyl group, one has the tauryl derivatives of Formula I compounds.

Preferred compounds include carnosine and homocarnosine; and N-acetyl, methylated (anserine, ophidine), decarboxylated (carcinine) and tauryl derivates of carnosine and homocarnosine. Of these compounds, carnosine and its pharmaceutically acceptable salts, hydrates, or prodrug formulations is highly preferred.

Use of both L and D isomers of carnosine and other compounds of Formula I, and mixtures thereof, are also contemplated by the present invention.

Carnosine

Over a hundred years ago, Gulewitsch and Amiradzibi successfully isolated a crystalline substance from Liebig's meat extract, which they called carnosine, the first peptide isolated from natural material. Bakardjiev, A. and Bauer, K., *Biochemistry* (Mosc) 2000 July; 65(7):779-82. Carnosine, a dipeptide, is synthesized from beta-alanine and histidine by the enzyme carnosine synthase Bakardjiev, A. and Bauer, K., *Biochemistry* (Mosc) 2000 July; 65(7):779-82., present in both neurons and glia. De Marchis, S. et al., *Biochemistry* (Mosc). 2000 July; 65(7):824-33. Other omega-aminoacyl amino acids are also synthesized by carnosine synthase, an enzyme with broad substrate specificity. Bakardjiev, A. and Bauer, K., *Biochemistry* (Mosc) 2000 July; 65(7):779-82. β-Alanine, a non-proteinogenic amino acid, is produced mainly by the liver as the final metabolite of uracil and thymine degradation. Carnosine is digested not by regular peptidases, but by a specific enzyme, carnosinase. Boldyrev, A. A. *Biochemistry* (Mosc) 2000; 65: 751-756.

Carnosine, a commercially available compound, has the chemical formula $C_9H_{14}N_4O_3$, and specifically L-carnosine has the chemical name β-Alanlyl-L-histidine. Turner has outlined the chemical synthesis of carnosine and other Formula I compounds. Quinn, P. J. et al., *Molec. Aspects Med*. 13:379-444 (1992). Carnosine and anserine can also be isolated efficiently from red muscle tissue by forming an aqueous extract and subsequent alcohol precipitation. Quinn, P. J. et al., *Molec. Aspects Med*. 13:379-444 (1992). U.S. Pat. No. 4,359,416 describes a process for preparing L-carnosine.

Carnosine and other histidine-containing dipeptides are abundant in vertebrate tissues including brain, heart and skeletal muscles. Stvolinsky, S. L. and Dobrota, D. *Biochemistry* (Mosc) 2000; 65: 849-855. Carnosine's greatest presence in the body is in muscles, where its principal role appears to be as a buffer. Carnosine may act to accept protons released by lactic acid during glycolysis. Stvolinsky, S. L. and Dobrota, D. *Biochemistry* (Mosc) 2000; 65: 849-855. In 1974, researchers first determined that carnosine is present in the olfactory bulb and nasal olfactory epithelium of rodents at concentrations higher than any other brain region. De Marchis, S. et al., *Biochemistry* (Mosc). 2000 July; 65(7): 824-33; see also Kish, S., J Neurochem 1979 June; 32(6): 1629-36. Since then, most studies performed on omega-aminoacyl amino acids in the mammalian nervous system have focused on their occurrence and possible function in this brain region. De Marchis, S. et al., *Biochemistry* (Mosc). 2000 July; 65(7):824-33.

Bakardjiev and Bauer report that immunolocalization studies suggest that, in brain regions outside the olfactory bulb, carnosine and its relatives are associated with glial cells. (Bakardjiev and Bauer Biochemistry (Mosc) 2000 July; 65(7):779-82) These data agree with studies on the biosynthesis of carnosine by primary cultures of rodent brain-derived glial cells. Bakardjiev and Bauer used highly enriched cultures of astrocytes and oligodendrocytes to demonstrate that this carnosine synthesis is restricted to the oligodendrocytes. Bakardjiev, A. and Bauer, K., *Biochemistry* (Mosc) 2000 July; 65(7):779-82. In the olfactory system, neurons also contain carnosine. Trombly, P. Q., et al., *Biochemistry* (Mosc) 2000; 65:897-816. The almost complete overlap of glial fibrillary acidic protein and carnosine immunoreactivity, and the ability of cultured rat glial cells to synthesize carnosine suggest most carnosine-containing cells are astrocytes, oligodendrocytes, or ensheathing cells. Trombly, P. Q., et al., *Biochemistry* (Mosc) 2000; 65:897-816.

The precise roles and mechanisms of action of carnosine are not well understood. (see Bakardjiev and K. Bauer *Biochemistry* (Mosc) 2000 July; 65(7):779-82, De Marchis, S. et al., *Biochemistry* (Mosc). 2000 July; 65(7):824-33.). Carnosine is recognized for its antioxidant and proton buffer properties, protection against oxidative stress, and resistance towards senescence. Stuerenburg, H. J., *Biochemistry* (Mosc) 2000; 65: 862-865; Hipkiss, A. R., et al., *Biochemistry* (Mosc) 2000; 65: 771-8; Hipkiss, A. R. and Brownson, C. *Cellular and Molecular Life Sciences* 2000; 57: 747-753; Wang, A. M., et al., *Biochemistry* (Mosc) 2000; 65: 869-71; Gallant, S., et al., *Biochemistry* (Mosc) 2000; 65: 866-868. Stvolinsky, S. L. and Dobrota, D. *Biochemistry* (Mosc) 2000; 65: 849-855; Holliday, R. and McFarland, G. A. *Biochemistry* (Mosc) 2000; 65: 843-848; Boldyrev, A. A. *Biochemistry* (Mosc) 2000; 65: 751-756; Abe, H., *Biochemistry* (Mosc) 2000; 65: 757-765

Stvolinsky and Dobrota report that carnosine enhances the resistance of animals towards ionizing radiation, hypobaric hypoxia, and supercooling, both decreasing mortality and improving recovery. *Biochemistry* (Mosc) 2000; 65: 849-855. Quinn reports several other medical uses for carnosine including ones associated with carnosine's reported antihypertensive effects, immunological effects, wound healing, cataract and lens effects, and antineoplastic effects. Quinn, P. J. et al., *Molec. Aspects Med*. 13:379-444 (1992). Carnosine has also been reported to have anti-ischemic and stroke effects, possibly due to its antioxidant, proton buffering, metal chelation, and macrophage regulation properties. Stvolinsky, S. L. and Dobrota, D. *Biochemistry (Mosc)* 2000; 65: 849-855., Stvolinsky, S. L. et al., *Cell Mol Neurobiol* 19(1): 45-56 (1999). When carnosine is complexed with copper and zinc ions the resulting compounds have been reported to have superoxide dismutase activity. *Biochemistry (Mosc)* 2000; 65: 849-855. Stvolinsky and Dobrota also report that carnosine has been demonstrated to be both an efficient immunomodulator and anti-inflammatory agent. *Biochemistry (Mosc)* 2000; 65: 849-855.

One of carnosine's earliest medical uses was as a complex with zinc for treating peptic ulcers. In U.S. Pat. No. 4,981, 846, "Crystalline L-carnosine zinc complex having antiulcer activity," Matsukura described a form of zinc that, relative to amorphous zinc complex, had higher purity, greater stability, and higher anti-ulcer activity. Matsukura and Tanaka reported a zinc-carnosine complex (L-CAZ; generic name Polaprezinc) as "the first drug for oral administration in which zinc plays an essential role." Matsukura, T., and Tanaka, H. *Biochemistry (Mosc)* 2000; 65:817-823. L-CAZ inhibited *Helicobacter pylori*, Matsukura, T., and Tanaka, H. *Biochemistry (Mosc)* 2000; 65:817-823, a cause of many ulcers. Yoshikawa reports on zinc-carnosine's antiulcer effects in the context of its reported antioxidant properties. *Free Radic Res Commun.* 1991; 14(4):289-96.

Carnosine will also complex with endogenous transitional metals of biological significance. Matsukura, T., and Tanaka, H. *Biochemistry (Mosc)* 2000; 65:817-823. Trombly, P. Q., et al., *Biochemistry (Mosc)* 2000; 65:897-816; Matsukura, T., and Tanaka, H. *Biochemistry (Mosc)* 2000; 65:817-823; Kohen, R., et al., *Free Radical Research Communications* 1991; 1:179-85; Homing, M. S., et al., *Brain Research* 2000; 852: 56-61; Baran, E. J., *Biochemistry (Mosc)* 2000; 65: 789-797. Stvolinsky, S. L. and Dobrota, D. *Biochemistry (Mosc)* 2000; 65: 849-855., Boldyrev, A. and Abe, H., *Cellular and Molecular Neurobiology*, 19, 163-175 (1999), Quinn, P. J. et al., *Molec. Aspects Med.* 13:379-444 (1992). Trombley reports that while carnosine may not act directly act as a neurotransmitter, research suggests that it may be a modulator of neurotransmitters, by influencing how zinc and copper ions interact with synaptic receptors. Trombly, P. Q., et al., *Biochemistry (Mosc)* 2000; 65:897-816. Homocarnosine may also modulate synaptic transmission by controlling zinc availability. Petroff, O. A. C. et al., *Neurology* 2001; 56:709-715. Zinc and copper have been found in pools in brain regions (hippocampus, locus ceruleus, hypothalamus, olfactory bulb, and cortex) at concentrations that allow them to exert neuromodulator effects. Trombly, P. Q., et al., *Biochemistry (Mosc)* 2000; 65:897-816.

While these transition metals are required for normal functioning of the nervous system, they have also been found to be neurotoxic. Trombly, P. Q., et al., *Biochemistry (Mosc)* 2000; 65:897-816; Horning, M. S., et al., *Brain Research* 2000; 852: 56-61. Shifts in zinc and copper may be involved in the neuropathy of Alzheimer's disease, ischemic stroke, and seizures. 37, Trombly, P. Q., et al., *Biochemistry (Mosc)* 2000; 65:897-816. Further, zinc and copper have been shown to suppress GABA-mediated inhibitory synaptic transmission. Carnosine can also prevent the influx of copper and zinc and enhance GABA function. Horning, M. S., et al., *Brain Research* 2000; 852: 56-61.

Russian scientists studied antispasmodic and angioprotector effects of carnosine in a rat model genetically predisposed to audiogenic epilepsy, associated with extended hemorrhaging. By injecting carnosine prior to acoustic stress, the researchers reportedly observed moderation of such seizures. Stvolinsky, S. L. and Dobrota, D. *Biochemistry (Mosc)* 2000; 65: 849-855. Bondarenko has reported that homocarnosine protects against the convulsions experienced by animals subject to hyperbaric oxygen and, that after exposure to hyperoxia, rabbits' concentration of homocarnosine is diminished in rabbits after hyperoxia. Kohnen, R. et al., *Proc. Natl. Acad. Sci. USA* 85:3175-3179 (1988).

Carnosine may have some beneficial effect on Alzheimer's patients (see Trombly, P. Q., et al., *Biochemistry (Mosc)* 2000; 65:897-816.). In addition to chelation discussed above, such an effect may be attributable to carnosine's antiglycosylation abilities. Carnosine, in high concentration, can even reverse protein-aldehyde cross-linking. Boldyrev, A. A. *Biochemistry (Mosc)* 2000; 65: 751-756.

The exact metabolic roles of carnosine and other Formula I compounds remain obscure. Bakardjiev, A. and Bauer, K., *Biochemistry (Mosc)* 2000 July; 65(7):779-82., Quinn, P. J. et al., *Molec. Aspects Med.* 13:379-444 (1992), De Marchis, S. et al., *Biochemistry (Mosc)*. 2000 July; 65(7):824-33. Many claims associated with carnosine are weakly supported, and there is a need for more rigorous, controlled clinical and experimental studies of carnosine's effects. Quinn, P. J. et al., *Molec. Aspects Med.* 13:379-444 (1992).

Formulation of carnosine (or other Formula I compounds) with certain metal cations (e.g., zinc or copper) or certain vitamins (e.g., vitamin B6, vitamin E) or pro-vitamins is specifically contemplated by the present invention.

Other Formula I Compounds

Carnosine's methylated derivatives, anserine and ophidine are hydrolyzed much more slowly then the parent compound. Boldyrev, A. A. *Biochemistry (Mosc)* 2000; 65: 751-756. Homocarnosine, carcinine, and N-acetylcarnosine have negligible rate of hydrolysis. Boldyrev, A. A. *Biochemistry (Mosc)* 2000; 65: 751-756. Metabolic transformation can then protect carnosine against enzymatic hydrolysis. Boldyrev, A. A. *Biochemistry (Mosc)* 2000; 65: 751-756.

Methylation at N1 position of the imidazole ring forms anserine, whereas methylation at N3 forms ophidine. Boldyrev, A. and Abe, H., *Cellular and Molecular Neurobiology*, 19, 163-175 (1999) In vivo acetylation of carnosine and anserine occurs in some animals. Boldyrev, A. and Abe, H., *Cellular and Molecular Neurobiology*, 19, 163-175 (1999) O'Dowd discusses the procurement, synthesis and study of N-acetyl derivatives of carnosine. Carnosine upon decarboxylation becomes carnicine. Boldyrev, A. and Abe, H., *Cellular and Molecular Neurobiology*, 19, 163-175 (1999), Quinn, P. J. et al., *Molec. Aspects Med.* 13:379-444 (1992). Fontana and coworkers discuss synthesis of tauryl carnosine derivatives, i.e. sulphonamide pseudopeptides. Fontana M, et al, *Cell Mol Life Sci* 2002 March; 59(3):546-51.

Homocarmosine has the chemical formula $C_{10}H_{16}N_4O_3$, and specifically L-homocarnosine has the chemical name γ-Aminobutyryl-L-histidine. Anserine, methylation on N1 of the imidazole ring, has the chemical formula $C_{10}H_{16}N_4O_3$, and specifically L-anserine has the chemical name β-Alanlyl-1-methyl-L-histidine. Ophidine, methylation on N3 of the imidazole ring, has the chemical formula $C_{10}H_{16}N_4O_3$, and specifically L-ophidine has the chemical name β-Alanlyl-3-methyl-L-histidine.

Homocarnosine is a dipeptide synthesized from Gamma-aminobutyric acid (GABA) and histidine. GABA itself acts as a major inhibitory chemical used by the body. GABA is the major inhibitory neurotransmitter in the cortex. Bradford, H. F., *Progress in Neurobiology* 1995, 47:477-511; Meldrum, B. S. *International Review Neurobiology* 1975; 17:1-36. GABA has the ability to control seizure activity. Pyrrolidinone, the internal lactam of GABA, crosses the blood brain barrier more readily than GABA and also has anticonvulsant activity. Petroff, O. A. C. et al., *Neurology* 2001; 56:709-715. According to an article published in Neurology, "inherited and acquired defects in GABA synthesis result in low GABA levels and are associated with epilepsy." Peltola J, Neurology 2000; 55: 46-50. In man, both inherited and acquired defects in GABA synthesis result in low GABA levels and are associated with epilepsy. Petroff, O. A. C. et al., *Neurology* 2001; 56:709-715. Low GABA levels are observed in patients with frequent complex partial seizures. Petroff, O. A. C. et al., *Neurology* 2001; 56:709-715. However, whether or not low GABA levels are a result or a cause of seizures is not known. Henry, T. R., et al., Neurology, 56:698-99 (2001).

Homocarnosine was first identified in 1961 in cow brain. Takahashi, H., *Brain Development* 1981; 3: 263-270. Homocarnosine levels change with age. Takahashi, H., *Brain Development* 1981; 3: 263-270. Homocarnosine may act directly on GABA receptors or indirectly after it is broken down into its primary components, GABA and histidine. Petroff, O. A. C. et al., *Neurology* 2001; 56:709-715. Homocarnosine has anticonvulsant properties with several potential mechanisms of action. Petroff, O. A. C. et al., *Neurology* 2001; 56:709-715. Regardless of its mechanism of action, it is shown that elevated homocarnosine levels in the occipital lobe of the brain are correlated with good seizure control. According to a study conducted by Ognen A. C. Petroff, M. D., "Studies in patients with complex partial seizures suggest that above normal levels of CSF (cerebral spinal fluid) and occipital lobe homocarnosine may contribute to improved seizure control . . . . Low homocarnosine was associated with poor seizure control and higher levels with better control." Neurology 2001; 56: 709-15.

Whether elevated levels of homocarnosine help to prevent seizures or whether such levels are merely a sign of better seizure control is a difficult question to answer. Henry, T. R., et al., Neurology, 56:698-99 (2001). Compared to primates, most epilepsy models, including rodents and other nonprimate organisms have lower brain homocarnosine concentrations and far less homocarnosinase activity. Henry, T. R. et al., Neurology 56:698-99 (2001). Accordingly, generation of GABA would be expected to be much slower in such animals, T. R. et al., *Neurology* 56:698-99 (2001). Studies on level of homocaronsine and epilepsy/seizures have been contradictory Takahashi, H., *Brain Development* 1981; 3: 263-270.

Recent work by Petroff and his colleagues at Yale University has demonstrated that GABA activity can be measured using MRI spectroscopy with higher field strength. Petroff, O. A. C. et al., *Neurology* 2001; 56:709-715. Although Petroff studied cases of generalized myoclonic epilepsies, his finding is significant because of the correlation established between levels of GABA and homocarnosine levels. Even in cases of low GABA function, homocarnosine levels may correlate with better seizure control. Cases of temporal lobe or generalized seizures have also shown seizure control to correlate to homocarnosine levels. Petroff, O. A. C. et al., *Neurology* 2001; 56:709-715.

Petroffs study, *Neurology* 56(6): 698-99 (2001), analyzed the relationship between seizure control and GABA, homocarnosine and pyrrolidinone levels in the visual cortex of patients with epilepsy taking valproate or lamotrigine. Previous studies suggested that poor seizure control was associated with low GABA and homocarnosine levels. Petroff and coworkers measured levels using HI NMR. Twenty-six adults were involved in the study (including 8 men). The researchers concluded that low GABA levels are associated with poor seizure control in patients with complex partial seizures, but not in juvenile myoclonic epilepsy patients. Higher homocarnosine levels are associated with better seizure control in both types of epilepsy. Petroff also notes, "Better seizure control was associated with higher homocarnosine levels in all patients taking valproate or lamotrigine."

Takahashi's reported that high homocarnosine levels in the cerebrospinal fluid of children with uncontrolled epilepsy or febrile convulsion may indicate the reduced turnover rate from homocarnosine to GABA. Takahashi, H., *Brain Development* 1981; 3: 263-270. Homocarnosine in cerebrospinal fluid may be related to convulsive tendency and consciousness. Takahashi made reference to Hayashi who reported the anticonvulsive effect of homocarnosine administered directly to the brain. Anticonvulsants may affect the enzymes involved in the synthesis and degradation of homocarnosine. Takahashi, H., *Brain Development* 1981; 3: 263-270. Drugs that are known to increase homocarnosine (vigabatrin, gabapentin and topiramate) also increase GABA. Petroff, O. A. C. et al., *Neurology* 2001; 56:709-715.

Formulation of Formula I Compounds

Formula I compounds include pharmaceutically acceptable salts, particularly where a basic or acidic group is present in a Formula I compound. For example, when an acidic substituent, such as —COOH, is present, the ammonium, sodium, potassium, calcium and the like salts, are contemplated as preferred embodiments for administration to a biological host. When a basic group (such as amino or a basic heteroaryl radical, such as pyridyl) is present, then an acidic salt, such as hydrochloride, hydrobromide, acetate, maleate, palmoate, phosphate, methanesulfonate, p-toluenesulfonate, and the like, is contemplated as a preferred form for administration to a biological host.

Similarly, where an acid group is present, then pharmaceutically acceptable esters of the compound (e.g., methyl, tert-butyl, pivaloyloxymethyl, succinyl, and the like) are contemplated as preferred forms of the compounds, such esters being known in the art for modifying solubility and/or hydrolysis characteristics for use as sustained release or prodrug formulations.

In addition, some compounds may form solvates with water or common organic solvents. Such solvates are contemplated as well. Both L and D isomers of carnosine and other Formula I compounds are contemplated by the present invention. Racemic mixtures of Formula I compounds are also within the scope of the present invention.

Compounds of Formula I can be used directly to practice materials and methods of the invention, but in preferred embodiments, the compounds are formulated with pharmaceutically acceptable diluents, adjuvants, excipients, or carriers. The phrase "pharmaceutically or pharmacologically acceptable" refer to molecular entities and compositions that do not produce adverse, allergic, or other untoward reactions when administered to an animal or a human, e.g., orally, topically, transdermally, parenterally, by inhalation spray, vaginally, rectally, or by intracranial injection. (The term parenteral as used herein includes subcutaneous injections, intravenous, intramuscular, intracisternal injection, or infusion techniques. Administration by intravenous, intradermal, intramusclar, intramammary, intraperitoneal, intrathecal, retrobulbar, intrapulmonary injection and/or surgical implantation at a particular site is contemplated as well.) Generally, this will also entail preparing compositions that are essentially free of pyrogens, as well as other impurities that could be harmful to humans or animals. The term "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art.

The pharmaceutical compositions containing Formula I compounds may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any known method, and such compositions may contain one or more agents selected from the group consisting of sweetening agents, flavoring agents, coloring agents and preserving agents in order to provide pharmaceutically elegant and palatable preparations. Tablets may contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia; and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for controlled release.

Formulations for oral use may also be presented as hard gelatin capsules wherein the active ingredient is mixed with an inert solid diluent, for example, calcium carbonate, calcium phosphate or kaolin, or as soft gelating capsules wherein the active ingredient is mixed with water or an oil medium, for example peanut oil, liquid paraffin, or olive oil.

Aqueous suspensions may contain the active compounds in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyl-eneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active compound in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compositions may also be in the form of suppositories for rectal administration of the PTPase modulating compound. These compositions can be prepared by mixing the drug with a suitable non-irritating excipient that is solid at ordinary temperatures but liquid at the rectal temperature and will therefore melt in the rectum to release the drug. Such materials are cocoa butter and polyethylene glycols, for example.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial an antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Methods of Treatment

As one aspect, the invention provides methods of improving neurological function in a human subject comprising steps of identifying a human subject having at least one condition selected from the group consisting of: autism, epilepsy, seizures, pervasive developmental disorder, cerebral palsy, Tourette's Syndrome, attention deficit disorder, attention deficit hyperactive disorder, central auditory processing disorder, dyslexia, apraxia of speech, motor type apraxia, panic disorder, bipolar disorder, Down's Syndrome and Asperger's Syndrome; and administering to the human subject a composition comprising at least one Formula I compound or a pharmaceutically acceptable salt, hydrate, or prodrug thereof, wherein the composition is administered in an amount effective to improve neurological function in the human subject.

The identification of appropriate subjects involves selecting individuals who have been medically evaluated and determined to have one or more of the aforementioned list of conditions (or performing a medical and diagnosing one or more of the conditions). In one preferred embodiment, the human subjects are 0-18 years old, and patients 2-12 years old are highly preferred. Treatment of adults also is contemplated.

The composition is administered in an amount effective to improve neurological function in the human subject. While there are many criteria for evaluating neurological function, it will be apparent to clinicians that each of the conditions referred to above is associated with one or more characteristic neurological abnormalities or deficits, which can be evaluated by physical (e.g., EEG, MRI), social, and psychological tests. Improvements by any such standard evaluation is scored as improved neurological function. Likewise, many of the conditions are associated with undesirable symptoms or physical manifestations, and to lessen the severity or occurrence of one or more symptoms associated with a disease state or disorder is also scored as improving neurological function.

As indicated above, any form of administration and pharmaceutical composition is contemplated, with oral administration of pills, powders, capsules, liquids, or food additives being preferred. Those of ordinary skill in the art will readily optimize effective dosages and administration regimens as determined by good medical practice and the clinical condition of the individual patient, taking into account such considerations as therapeutic efficacy, risk of toxicity, and side-effects. Appropriate dosages may be ascertained through the use of established assays for determining blood clotting levels in conjunction with relevant dose-response data. The final dosage regimen will be determined by the attending physician, considering factors that modify the action of drugs, e.g., the drug's specific activity, severity of the damage and the responsiveness of the patient, the age, condition, body weight, sex and diet of the patient, the severity of any infection, time of administration and other clinical factors. As studies are conducted, further information will emerge regarding appropriate dosage levels and duration of treatment for specific diseases and conditions.

The frequency of dosing will depend on the pharmacokinetic parameters of the agents and the routes of administration. The optimal pharmaceutical formulation will be determined by one of skill in the art depending on the route of administration and the desired dosage. See for example Remington's Pharmaceutical Sciences, 18th Ed. (1990, Mack Publ. Co, Easton Pa. 18042) pp 1435-1712, incorporated herein by reference. Such formulations may influence the physical state, stability, rate of in vivo release and rate of in vivo clearance of the administered agents. Depending on the route of administration, a suitable dose may be calculated according to body weight, body surface areas or organ size. Further refinement of the calculations necessary to determine the appropriate treatment dose is routinely made as part of any medical treatment regimen, especially in light of the dosage information and assays disclosed herein as well as the pharmacokinetic data observed in animals or human clinical trials Using carnosine as an example, administering 100-200 mg daily to a subject, or administering between 200 mg and 2000 mg per day, or administering 100 mg to 5000 mg, or administering between 100 mg and 250 mg per day, or administering 400 mg twice daily are just a few of the contemplated embodiments. The method of administration may be oral, topical, intraperitoneal, subcutaneous, sublingual, by inhaler, or other means.

In a preferred embodiment, the invention provides a method of improving neurological function in a human subject comprising identifying a human subject having at least one condition selected from the group consisting of: autism, epilepsy, seizures, pervasive developmental disorder, cerebral palsy, Tourette's Syndrome, attention deficit disorder, attention deficit hyperactive disorder, central auditory processing disorder, dyslexia, apraxia of speech, motor type apraxia, panic disorder, bipolar disorder, Down's Syndrome and Asperger's Syndrome; and administering to the human subject a composition comprising at least one compound selected from the group consisting of carnosine, homocarnosine, anserine, ophidine, carcinine, N-acetyl-carnosine, N-acetyl-homocarnosine, N-acetyl-anserine, N-acetyl-ophidine, and N-acetyl-carnicine.

In a highly preferred embodiment, the invention provides a method of improving neurological function of a human subject comprising identifying a human subject in need of treatment for at least one condition selected from the group consisting of: autism, epilepsy, seizures, pervasive developmental disorder, and cerebral palsy; and administering to the human subject a composition comprising carnosine in an amount effective to improve neurological function in the human subject.

In a very highly preferred embodiment, the condition is autism or epilepsy, and the compound is carnosine. Oral administration of the carnosine is preferred. With respect to epilepsy, specifically contemplated is treatment of intractable forms of epilepsy, meaning forms which have failed to respond to two or more treatment regiments using approved anticonvulsant/antiepileptic drugs.

Pharmaceutical (medicinal)treatment options exist for many of the aforementioned neurological conditions, which offer varying degrees of relief depending on the patient and the condition treated. It is contemplated that the Formula I compounds can be used together with such medicines to improve efficacy. Improved efficacy can be any measurable improvement for the human subject observed as a consequence of the combination therapy. For example, further improvement in neurological function, as described more fully above, is scored as improvement of the efficacy of the medicine. Likewise, since many medicines are both expensive and exert physical and/or behavioral side effects, the ability of co-administration of a Formula I compound to reduce the effective dose of a medicine is also scored as improving efficacy of the medicine, especially if the reduced dose results in reduced side-effects.

By way of example, the invention provides a method of increasing the efficacy of anticonvulsant medication, comprising administering to a human subject having epilepsy or a seizure disorder (or any other disorder for which anticonvulsants are prescribed) anticonvulsant medication and a composition comprising at least one Formula I compound, or a pharmaceutically acceptable salt, hydrate, or prodrug thereof, wherein the compound is administered in an amount effective to increase the efficacy of the anticonvulsant.

For this and other co-administration methods of the invention, the Formula I compound can be administered separately from or concurrently with the medication, and can also be admixed with the medication prior to administration.

Exemplary anticonvulsants/antiepileptics (AEDs) include, but are not limited to the following drugs, the formulation of which is known in the art and/or published in patent and trade literature:

Anticonvulsants/Antiepileptics (AEDS) (anticonvulsant medication) include, but are not limited to the following drugs:

| Brand Name | Generic Name | Patent (U.S. unless specified) |
|---|---|---|
| Carbatrol | Carbamazepine | 2,948,718 |
| Depakene | Valproic Acid | 3,325,361 |
| Depakote | Valproic Acid | 3,325,361 |
| Dilatin | Phenytoin | 2,409,754 |
| Felbatol | Felbamate | 288444; 4,978,680 |
| Gabitril | Tiagabine | 5,354,760 |
| Klonopin | Clonazepam | 3,121,076 |
| Lamictal | Lamotrigine | 4,602,017 |
| Mysoline | Primidone | 4,024,175 |
| Neurotonin | Gabapentin | 6,054,482 |
| Phenobarbital | Phenobarbital | 1,025,872 |
| Tegretol | Carbamazepine | 2,948,718 |
| Trileptal | Oxycarbozine | |
| Topomax | Topiramate | 4,513,006 |
| Zarontin | Ethosuximide | |
| Mesantoin | mephenytoin | |
| Peganone | ethotoin | |
| Mebaral | mephobarbital | |
| Keppra | levetiracetam | |
| Sabril | vigabatrin | |
| Diastat | diazepam | |
| Valium | diazepam | |
| Ativan | lorazepam | |
| | trimethadione | |
| | Gama-vinyl GABA | |
| | GABA | |
| Diamox | acetazolamide | |
| Tranxene | clorazepate | |
| | acetylpheneturide | |
| | albutoin | |
| Cytadren | aminoglutethimide | |
| | atrolactamide | |
| | beclamide | |
| | buramate | |
| | calcium bromide | |
| | cinoramide | |
| | clomethiazole | |
| | decimemide | |
| | diethadione | |
| | dimetadione | |
| | doxenitoin | |
| | eterobarb | |
| | ethadione | |
| | fluoresone | |
| Cerebyx | fosphenytoin | |
| | ganaxolone | |
| | magnesium bromide | |
| Epsom salt granules | magnesium sulfate | |
| Mebaral | mephobarbital | |
| | metharbital | |
| | methetoin | |
| Celontin Kapseals | methsuximide | |
| Versed | midazolam | |
| | narcobarbital | |
| Milontin Kapseals | nitrazepam | |
| | oxcarbazepine | |
| | paramethadione | |
| | phenacemide | |
| | phenetharbital | |
| | pheneturide | |
| | phensuximide | |
| | phenylmethylbarbituric acid | |
| | phethenylate sodium | |
| | potassium bromide | |
| | pregabalin | |
| | progabide | |
| | remacemide | |
| | rufinamide | |
| | sodium bromide | |
| | solanum | |
| | strontium bromide | |
| | suclofenide | |
| | sulthiame | |
| | talampanel | |
| | tetrantoin | |
| Tridione | trimethadione | |
| | valpromide | |
| Zonegran | zonisamide | |

In a preferred embodiment, the Formula I compound is carnosine.

Also in a preferred embodiment, the anticonvulsant medication comprises at least one member selected from the group consisting of carbamazepine, phenytoin, mephenytoin, ethotoin, mephobarbital, phenobarbital, primidone, valproate, gabapentin, lamotrigine, clonazepam, clorazepate, diazepam, lorazepam, ethosuximide, trimethadione, gama-vinyl GABA, GABA, acetazolamide, felbamate, tiagabine, levetiracetam, vigabatrin, and topiramate. In a highly preferred embodiment, the anticonvulsant medication comprises at least one member selected from the group consisting of: carbamazepine, valproic acid, phenyloin, febamate, tiagabine, clonazepam, lamotrigine, primidone, gabapentin, phenobarbital, oxycarbazine, topiramate and ethosuximide. In a very highly preferred embodiment, the anticonvulsant medication comprises at least one member selected from the group consisting of valproate and lamotrigine.

In another variation, the invention provides a method of increasing the efficacy of selective serotonin reuptake inhibitor (SSRI) medication, comprising administering to a human subject having a neurological disorder a selective serotonin reuptake inhibitor medication and a composition comprising at least one Formula I compound, or a pharmaceutically acceptable salt, hydrate, or prodrug thereof, wherein the compound is administered in an amount effective to increase the efficacy of the selective serotonin reuptake inhibitor.

Exemplary SSRI agents that are employed in SSRI medications include the following:

Selective Serotonin Reuptake Inhibitors (Selective Serotonin Reuptake Inhibitor (SSRI) Medication)

| Brand Name | Generic Name | Patent Number (U.S., unless specified) |
|---|---|---|
| Anafranil | Clomipramine hydrochloride | Swiss 371,799 |

-continued

| Brand Name | Generic Name | Patent Number (U.S., unless specified) |
|---|---|---|
| Celexa | Citalopram hydrobroide | 4,136,193 |
| Effexor | Velafaxine hydrocholoride | 4,535,186 |
| Luvox | Fluvoxamine maleate | 4,085,225 |
| Paxil | Paroxetine hydrocholoride | 3,912,749; 4,007,196 |
| Prozac | Fluoxetine hydrochloride | 4,314,081 |
| Zoloft | Setraline hydrocholoride | 4,536,518 |
| | Femoxetine | |
| | Indalpine | |
| | Indeloxazine Hydrocholoride | |
| | milnacipran | |
| | zimeldine | |

In a preferred embodiment, the selective serotonin reuptake inhibitor medication comprises at least one compound selected from the group consisting of clomipramine hydrochloride, citalopram hydrobromide, venlafaxine hydrochloride, fluvoxamine maleate, paroxetine hydrochloride, fluoxetine hydrochloride, and setraline hydrochloride.

In still another variation, the invention provides a method of increasing the efficacy of acetylcholinesterase inhibitor medication, comprising: administering to a human subject having a neurological disorder acetylcholinesterase inhibitor medication and a composition comprising at least one Formula I compound or a pharmaceutically acceptable salt, hydrate, or prodrug thereof, wherein the compound is administered in an amount effective to increase the efficacy of the acetylcholinesterase inhibitor medication. Exemplary acetylcholinesterase inhibitors include the following:

Acetylcholinesterase Inhibitors
(Acetylcholinesterase (ACE) Inhibitor Medication)

| Brand Name | Generic Name | Patent (U.S. unless specified) |
|---|---|---|
| Aricept | Donepezil Hydrochloride | 5,985,864 |
| Exelon | Rivastigmine | 4,948,807 |
| Reminyl | Galantamine | |
| | alacepril | |
| Lotensin | benazepril | |
| Capoten | captopril | |
| | ceronapril | |
| | cilazapril | |
| | delapril | |
| Vasotec | enalapril | |
| Vasotec I.V. | enalaprilat | |
| Monopril | fosinopril | |
| | imidapril | |
| | lisinopril | |
| Univasc | moexipril | |
| | moveltipril | |
| | omapatrilat | |
| Aceon | perindopril | |
| Accupril | quinapril | |
| Altace | ramipril | |
| | sampatrilat | |
| | sprirapril | |
| | temocaptril | |
| Mavik | trandolapril | |

In another embodiment, this invention encompasses a method of increasing the efficacy of pervasive developmental disorder medication. For example, such method involves administering to a human subject having a pervasive developmental disorder at least one pervasive developmental disorder medication and at least one Formula I compound, wherein the compound is administered in an amount effective to increase the efficacy of the pervasive developmental disorder medication. A pharmaceutically acceptable salt, hydrate, or prodrug of the Formula I compound or drug can also be used in the aforementioned method. Pervasive developmental disorder medications include, but are not limited to the following drug categories: anticonvulsants (AEDs), selective serotonin reuptake inhibitors and acetylcholinesterase inhibitors.

In another embodiment, this invention encompasses a method of increasing the efficacy of attention deficit/hyperactive disorder medication. This method involves administering to a human subject having a attention deficit/hyperactive disorder at least one attention deficit/hyperactive disorder medication and a composition comprising at least one Formula I compound, wherein the compound is administered in an amount effective to increase the efficacy of the attention deficit/hyperactive disorder medication. A pharmaceutically acceptable salt, hydrate, or prodrug of the Formula I compound or drug can also be used in the aforementioned method. Attention deficit/hyperactive disorder medications include, but are not limited to the following drugs: atomoxetine, clonidine, dextroamphetamine, pemoline and methylphenidate.

In still another embodiment, this invention encompasses a method of increasing the efficacy of stimulants. This method involves administering to a human subject having a neurological disorder at least one stimulant and a composition comprising at least one Formula I compound, wherein the compound is administered in an amount effective to increase the efficacy of the stimulant. A pharmaceutically acceptable salt, hydrate, or prodrug of the Formula I compound or drug can also be used in the aforementioned method. Stimulants include, but are not limited to the following drugs: amineptine, amphetamine, amphtaminil, bemegride, benphetamine, brucine, caffeine, chlorphentermine, clofenciclan, clortermine, coca, demanyl phosphate, deoxadrol, dextroamphetamine sulfate, N-ethylamphetamine, ethamivan, etifelmin, etryptamine, fencamfamine, fenethylline, fenozolone, flurothyl, hexacyclonate sodium, homlocamfin, inazindol, inefexamide, methamphetamine, methylphenidate, niketha- mide, pemoline, pentylenetetrazole, phendirmetrazine, phenmetrazine, phentermine, picrotoxin, pipradrol, prolintane and pyrovalerone.

Compositions of Matter

In yet another aspect, the invention includes compositions of matter that are useful for improving neurological functions in human subjects, particularly human subjects having neurological conditions discussed herein.

For example, the invention includes a composition comprising a neuromodulator, selected from the group consisting of anticonvulsant medication, selective serotonin reuptake inhibitor medication, acetylcholinesterase medication, pervasive developmental disorder medication, attention deficit disorder/attention deficit hyperactive disorder (ADD/ADHD) medication, and stimulant medication in admixture with a Formula I compound, or a pharmaceutically acceptable salt, hydrate, or prodrug thereof. Preferred Formula I compounds are carnosine, homocarnosine, anserine, ophidine, carcinine, N-acetyl-carnosine, N-acetyl-homocarnosine, N-acetyl-anserine, N-acetyl-ophidine, and N-acetyl-carnicine. A highly preferred Formula I compound is carnosine.

In a preferred variation, the composition further comprises a pharmaceutically acceptable diluent, adjuvant, excipient, or carrier, to facilitate and improve administration to a human subject. Pharmaceutical formulation chemistry is a well developed art, and exemplary formulation materials and methods are discussed above. Moreover, most approved medications in the categories set forth above have already been formulated effectively for administration to humans. In one embodiment, it is contemplated that such formulations be minimally modified to include the Formula I composition in a stable manner.

The Formula I composition is preferably included in the composition in an amount effective to improve the efficacy of the medication, using parameters for evaluation such as those described elsewhere herein.

In one preferred variation, the neuromodulator comprises at least one anticonvulsant selected from the group consisting of carbamazepine, phenytoin, mephenytoin, ethotoin, mephobarbital, phenobarbital, primidone, valproate, gabapentin, lamotrigine, clonazepam, clorazepate, diazepam, lorazeparn, ethosuximide, trimethadione, gama-vinyl GABA, GABA, acetazolamide, felbamate, tiagabine, levetiracetam, vigabatrin, and topiramate. Preferably, the Formula I compound is present in the composition in an amount effective to improve the therapeutic efficacy of the anticonvulsant medication in the treatment of seizures in a human subject.

In another preferred variation, the neuromodulator comprises at least one selective serotonin reuptake inhibitor selected from the group consisting of clomipramine hydrochloride, citalopram hydrobromide, venlafaxine hydrochloride, fluvoxamine maleate, paroxetine hydrochloride, fluoxetine hydrochloride, and setraline hydrochloride. Preferably, the Formula I compound is present in the composition in an amount effective to improve the therapeutic efficacy of the selective serotonin reuptake inhibitor medication in the treatment of seizures depression, obsessive-compulsive disorder or a panic disorder in a human subject.

In still another preferred variation, the neuromodulator comprises at least one acetylcholinesterase inhibitor selected from the group consisting of donepezil hydrochloride, rivastigmine and galantamine. Preferably, the Formula I compound is present in an amount effective to improve the therapeutic efficacy of the acetylcholinesterase inhibitor medication in a human subject.

In still another preferred embodiment, the neuromodulator comprises at least one pervasive developmental disorder medication selected from the group consisting of anticonvulsants (AEDs), selective serotonin reuptake inhibitors and acetylcholinesterase inhibitors. Preferably, the Formula I compound is present in an amount effective to improve the therapeutic efficacy of the pervasive developmental disorder medication in a human subject.

In still another preferred variation, the neuromodulator comprises at least one ADD/ADHD medication selected from the group consisting of atomoxetine, clonidine, dextroamphetamine, pemoline and methylphenidate. Preferably, the Formula I compound is present in an amount effective to improve the therapeutic efficacy of the ADD/ADHD medication in a human subject.

In yet another preferred variation, the neuromodulator comprises at least one stimulant selected from the group consisting of amineptine, amphetamine, amphtaminil, bemegride, benphetamine, brucine, caffeine, chlorphentermine, clofenciclan, clortermine, coca, demanyl phosphate, deoxadrol, dextroamphetamine sulfate, N-ethylamphetamine, ethamivan, etifelmin, etryptamine, fencamfamine, fenethylline, fenozolone, flurothyl, hexacyclonate sodium, homocarifin, mazindol, mefexamide, methamphetamine, methylphenidate, nikethamide, pemoline, pentylenetetrazole, phendimetrazine, phenmetrazine, phentermine, picrotoxin, pipradrol, prolintane and pyrovalerone. The Formula I compound preferably is present in an amount effective to improve the therapeutic efficacy of the stimulant medication in a human subject.

Carnosine may enable improved auditory processing and development, as well as, improved attention span. Carnosine may improve reading performance, memory or other neuropsychometric measures.

In still a related variation of the preceding embodiments, the medication (neuromodulator) is packaged or formulated together with the Formula I compound (e.g., in a kit or package or unit dose) to permit co-administration, but these two components are not in admixture. In a preferred embodiment, the two components to the kit/unit dose are packaged with instructions for administering the two agents to a human subject for treatment of one of the above-indicated diseases.

In still another related variation, the invention can be characterized as providing a new use for Formula I compounds. For example, the invention provides the use of one or more Formula I compositions (or a pharmaceutically acceptable salt, hydrate, or prodrug thereof) for the manufacture of a medicament for the treatment of at least one condition selected from the group consisting of autism, epilepsy, seizures, pervasive developmental disorder, cerebral palsy Tourette's Syndrome, attention deficit disorder, attention deficit hyperactive disorder, central auditory processing disorder, dyslexia, apraxia of speech, motor type apraxia, panic disorder, bipolar disorder, Down's Syndrome and Asperger's Syndrome. Preferred Formula I compounds include carnosine, homocarnosine, anserine, ophidine, carcinine, N-acetyl-carnosine, N-acetyl-homocarnosine, N-acetyl-anserine, N-acetyl-ophidine, and N-acetyl-carnicine. Carnosine is highly preferred, especially for manufacture of a medicament for the treatment of at least one condition selected from the group consisting of autism, epilepsy, seizures, pervasive developmental disorder, and cerebral palsy.

With respect to any such new uses of Formula I compounds, it will be apparent from the foregoing that the medicament will optionally additionally include one or more of the neuromodulator medicines that have been identified herein (e.g., anticonvulsant medications, selective serotonin reuptake inhibitor medications, acetylcholinesterase medications, pervasive developmental disorder medications, attention deficit disorder/attention deficit hyperactive disorder (ADD/ADHD) medications, and stimulant medications).

The full scope of this invention will be better appreciated after examination of the following illustrative examples, which are not meant to limit the scope of the invention.

Example 1

Oral Administration of Carnosine to Modulate the Central Nervous System

Epileptic activity may be inhibited by GABA, but certain patients seem deficient or resistant to GABA enhancing medication. It is hypothesized that carnosine may have anti-seizure effects as well as the ability to improve cognitive function. There are anti-seizure drugs available that secondarily elevate carnosine levels but as of now, there are no drugs available whose primary function is to elevate carnosine levels as a treatment for seizure disorders. Prior to the applicant's invention, carnosine has not been used as a treatment for seizure disorders. It is believed that by directly increasing carnosine levels, the number of seizures will decrease and the effectiveness of additional prescribed anti-convulsants will increase.

It is possible to increase central nervous system (CNS) carnosine levels by administering carnosine in the form of a simple dietary supplement. A gel capsule, composed of 100 mg of powdered carnosine with cellulose filler, will be taken orally at 100-200 mg/day. The carnosine dietary supplement has no known side effects. A carnosine supplement is now available in gel capsule form provided by the pharmaceutical company, Alfa Chem (Kings Point, N.Y.). It is believed that by supplementing carnosine, additional inhibitory neurotransmitters will be synthesized which will function to reduce the number of seizures, improve cognitive function, and increase the efficacy of prescribed anti-convulsants.

Example 2

Use of Carnosine to Improve Cognitive Functions Impaired by Neurological Disorders It is hypothesized that carnosine may improve cognitive functions of patients suffering from various disorders. These disorders include autism, pervasive developmental disorder, brain injury, cerebral palsy and epilepsy. There are currently no drugs or treatments available whose primary function is to elevate carnosine levels as a treatment for the previously mentioned disorders. Patients afflicted with the above disorders were treated with a dietary supplement of carnosine in dosages of 200 mg to 2,000 mg per day. The carnosine supplement is available in gel capsule form from Alfa Chem (Kings Point, N.Y.).

The carnosine supplement can be administered orally several times daily. The results indicated an increase in cognitive processing speed, an increase in language skills, and improved motor skills. Patients have increased their amount of speech and language and the level of maturity of speech. Receptive language has also improved.

It is believed that by supplementing carnosine in the patients suffering from the above disorders, additional inhibitory neurotransmitters will be synthesized which will function to reduce the number of seizures, improve cognitive functions, improve language and motor skills, and increase efficacy of prescribed anti-convulsants.

Example 3

Carnosine Improves Intractable Epilepsy Patients

L-carnosine is an amino acid dipeptide (histidine and alanine), that may indirectly affect spike and wave discharges by altering GABA bioavailability or affecting copper and zinc influx at the cellular level. MRI spectroscopy has recently demonstrated that brain homocarnosine levels may correlate with seizure control. We hypothesized that carnosine ingestion would modulate homocarnosine in the brain, causing spike and wave activity to decrease and seizure control to improve. We gave L-carnosine to four patents as add-on therapy for intractable spike-wave discharge and documented changes in both clinical (overt seizures) and physiological (EEG) status.

Methods

Seven children (3 female, 4 male, age range 2-12) met inclusion criteria. All had intractable seizures for at least two years, had failed at least 3 anticonvulsants, had documented, abnormal generalized or secondarily generalized spike-wave, atypical absence, or Lennox-Gastaut Syndrome. All families signed written consent from an IRB approved protocol. All children were evaluated with a Baseline EEG on the same day they were started on 400 mg b.i.d. of L-carnosine. Carnosine from, for example, Alfa Chem in either powder or capsule form. Carnosine may also be obtained from MAYPRO (Purchase, N.Y.), as well as various other suppliers. Post-treatment EEG was undertaken after 10 weeks of L-carnosine therapy. No other concurrent medications were changed. All patients had failed multiple medication treatments prior to the addition of carnosine. These medications included valproic acid, topimirate, benzodiazepines, steroids, carbamazepine, phenytoin, zonisamide, lamotrigine, and phenobarbital.

Results

After 10 weeks of carnosine therapy at 400 mg p.o. b.i.d., 5 of these 7 children had documented improved EEG findings. Changes included decreased frequency of polyspikes (2 children), improved secondarily generalized spike-wave activity (1 child), and improved background and decreased electrographic slow-spike and wave activity (2 children). No significant EEG changes occurred in 2 children. Seizure frequency improved in all 7 patients. Although not evaluated formally, improvements in the domains of global cognition, behavior, and language function were reported in all 7 patients. Those domains were not predicted to react to carnosine, and were elicited spontaneously via blinded therapists and family members who noted gains in areas not typically associated with the GABA-ergic system.

Conclusion

These data indicate that L-carnosine is a useful add-on medication for intractable seizure disorders with encephalopathic EEG changes or generalized epileptiform activity. Although the exact mechanism is unknown, L-carnosine is believed to bind with GABA to form homo-carnosine, and may also modulate copper and zinc influx into the neurons decreasing the after-discharges of spike-wave discharges. Further investigation of the effects and exact mechanisms of L-Carnosine is warranted.

Example 4

Carnosine to Improve Cognitive Function in Autistic Spectrum Disorders

Since carnosine has been described as accumulating in the enterorhinal subfrontal cortex, it is hypothesized that carnosine might act in a protective or activating role for the frontal lobe. Dysfunction of the frontal lobe is hypothesized to be linked to expression and behavior, both areas characteristically impaired in ASD.

The following protocol was designed to target the purported brain region of dysfunction in ASD, via supplementation with a naturally-occurring amino acid which is believed to act upon frontal lobe systems or GABA receptors. We sought to eliminate the "expectancy effect" of medication augmentation by enrolling children in a study so that both the clinicians and parents were blinded to group assignment.

Methods

Children were included for study if they met the following criteria: ages 3-12, prior diagnoses of Autistic Spectrum Disorder (including either Pervasive Developmental Disorder or Autistic Disorder, by DSMIVR). *American Psychiatric Association. Diagnostic and Statistical Manual of Mental Disorders,* 4th ed. Washington D.C., 1993. The subjects may have had a prior history of abnormal electroencephalogram and prior or current trial of valproic acid. Children were excluded if they had a family history of seizure disorder, Fragile X, or other genetic disorder or etiology of their spectrum disorder. Children were enrolled in the study irrespective of cognitive ability level.

All children were tested at baseline in the following domains: expressive language (Expressive One Word Picture Vocabulary test, EOWPVT), receptive language (Receptive One Word Picture Vocabulary test, ROWPVT), autism severity ratings (Childhood Autism Rating Scale; CARS, and Gilliam Autism Rating Scales; GARS), and Clinical Global linpresssions (CGI) completed by parents. At baseline and eight-week testing, all children underwent the CARS, GARS, EOWPVT, ROWPVT, and CGI. Schopler, E., Reichler, R. J., Renner, B. R. *The Childhood Autism Rating Scale: CARS.* Los Angeles, Calif.: Western Psychological Sciences 1988. Gilliam, J. E. *The Gilliam Autism Rating Scale: GARS.* Austin, Tex.: Pro-Ed Inc. 1995. Gardner, M. F. Receptive One-Word Picture Vocabulary Test: ROWPVT. Novato, Calif.: Academic Therapy Publications 1985. Gardner, M. F. Expressive One-Word Picture Vocabulary Test (Revised): EOWPVT-R. Novato, Calif.: Academeic Therapy Publication 1990. Children were tested with their parents in the room of a pediatric neurology clinic in a room dedicated to assessment. Parents signed informed written consent (approved by the Lake Forest Hospital Institutional Review Board) before being randomly assigned to either active agent or placebo, and reporting of adverse events was explained per office emergency policy. Because of our prior experience with the substance in an open-label format, we were able to caution regarding the following potential adverse events: hyperactivity, excitability Both placebo and active substance were identical in powdered appearance, without taste or smell. All pills were contained by a gelatin capsule; parents were instructed to mix the powder with either food or drink. Dosage of carnosine was 400 mg by mouth twice a day.

Every two weeks, parents faxed a CGI regarding their child. The CGI was a 5 point rating scale covering the following domains: (1) Socialization, interaction with others during play, (2) Spontaneous, expressive language or vocalizations, (3) Attention span, "focus"/eye contact, alertness level, (4) Agitation and hyperactivity or lethargy, energy level, Petroff, O. A. C. et al., *Neurology* 2001; 56:709-715. Coordination, body use, gross motor movements, (6) Anxiety, rigidity, preservation, adaptation to change. A score of "0" indicated "No Change", a score of "5" indicated a "Great improvement." Parents were not allowed to refer back to faxes from the prior two week period, so that each rating was essentially "blinded" to the week before. An overall baseline CGI was then compared with an ending CGI.

Results

Thirty-one children (21 M, mean age=7.45; range 3.2-12.5) meeting inclusion criteria were enrolled in an 8 week, double-blind placebo-controlled study. Children were entered randomly into one of two groups: Group I (n=17) received a placebo for the first 8 weeks, while Group II (n=14) received the active substance. Children were assessed at Baseline in the following domains:

TABLE 1

Baseline measures for children in blinded carnosine study.

|  | Placebo (n = 17) Mean (SD) | Active (n = 14) Mean (SD) | Significant? |
| --- | --- | --- | --- |
| Age (months) | 92.47 (28.95) | 85.69 (24.57) | NS |
| CGI | 12.94 (4.18) | 14.50 (3.65) | NS |

TABLE 1-continued

Baseline measures for children in blinded carnosine study.

|  | Placebo (n = 17) Mean (SD) | Active (n = 14) Mean (SD) | Significant? |
| --- | --- | --- | --- |
| EOWPVT (raw) | 30.65 (26.28) | 35.36 (20.87) | NS |
| EOWPVT (age-adjusted) | 35.41 (29.94) | 40.71 (23.44) | NS |
| ROWPVT (raw) | 34.29 (28.56) | 38.00 (23.67) | NS |
| ROWPVT (age-adjusted) | 39.65 (27.91) | 41.67 (24.04) | NS |
| CARS | 34.97 (6.69) | 31.71 (6.55) | NS |
| GARS | 50.88 (16.96) | 55.50 (16.35) | NS |
| Behavior Scale | 17.17 (8.71) | 15.71 (6.65) | NS |
| Socialization Scale | 18.47 (6.4) | 18.14 (6.23) | NS |
| Communication Scale | 15.23 (6.68) | 21.64 (7.99) | p = .02 |

There were no statistically significant differences in any of the baseline measures with the exception of the Communication subscale of the GARS. Although the group on the Active substance started out with a higher level on the Communication scale, there were not statistically significant differences when tested on the objective language measures, the ROWPVT and the EOWPVT. After 8 weeks, children returned for repeat testing. Below are the scores for the follow-up testing.

TABLE 2

Follow-up assessment of children on either active carnosine or placebo after 8 weeks.

|  | Placebo (n = 17) Mean (SD) | Active (n = 14) Mean (SD) | Significant? |
| --- | --- | --- | --- |
| CGI | 14.25 (4.50) | 16.39 (4.36) | NS |
| EOWPVT (raw) | 31.65 (29.19) | 37.28 (25.66) | NS |
| EOWPVT (age-adjusted) | 37.17 (33.38) | 43.78 (28.22) | NS |
| ROWPVT (raw) | 37.11 (30.89) | 44.64 (26.56) | NS |
| ROWPVT (age-adjusted) | 41.65 (30.45) | 47.85 (28.37) | NS |
| CARS | 33.76 (6.53) | 29.75 (7.53) | NS |
| GARS | 49.88 (16.79) | 44.36 (14.94) | NS |
| Behavior Scale | 15.82 (7.74) | 12.85 (5.95) | NS |
| Socialization Scale | 17.29 (7.78) | 13.36 (6.58) | NS |
| Communication Scale | 16.88 (6.48) | 18.14 (6.27) | NS |

As may be seen from Table 2, any changes-that occurred within the two groups did not result in two groups that looked characteristically different from each other at the end of the 8 week period. However, an examination of the changes that occurred within the active carnosine group illustrates that indeed there were meaningful changes after 8 weeks on the substance (see Table 3) on a case-by-case basis.

TABLE 3

Changes in children after 8 weeks on active carnosine.

|  | Baseline Mean (SD) | 8-Week Mean (SD) | Significant? |
| --- | --- | --- | --- |
| CGI | 14.50 (3.65) | 16.39 (4.36) | .06 |
| Fax ratings (week 2 vs. week 6) | 2.03 (2.24) | 4.92 (5.69) | .04 |
| EOWPVT (raw) | 35.36 (20.87) | 37.28 (25.66) | NS |
| EOWPVT (age-adjusted) | 40.71 (23.44) | 43.78 (28.22) | NS |
| ROWPVT (raw) | 38.00 (23.68) | 44.64 (26.56) | .01 |
| ROWPVT (age-adjusted) | 40.57 (24.55) | 47.86 (28.37) | .01 |
| CARS | 31.71 (6.55) | 29.75 (7.53) | .07 |
| GARS | 55.50 (16.35) | 44.35 (14.93) | .01 |
| Behavior Scale | 15.71 (6.65) | 12..86 (5.95) | .04 |

TABLE 3-continued

Changes in children after 8 weeks on active carnosine.

| | Baseline Mean (SD) | 8-Week Mean (SD) | Significant? |
|---|---|---|---|
| Socialization Scale | 18.14 (6.30) | 13.36 (6.58) | .01 |
| Communication Scale | 21.64 (7.99) | 18.14 (6.27) | .03 |

It is apparent from examining Table 3 that there were changes across several measures in multiple domains for those children who were given the carnosine for 8 weeks. In contrast, pairwise t-tests performed on the placebo group showed that there were no changes on any of the measures after 8 weeks on the inert pills (all p's<0.05).

Discussion

The results of this study indicate that supplementation with carnosine can significantly improve receptive speech, socialization, and behavior in children with autistic spectrum disorders. Data show better language receptivity, better autism score on GARS, as well as, better trends for expressive speech and CARS. These gains are observable both by parents and clinicians blinded to study group, as evidenced by the scores on the CGI and faxed rating scales. Moreover, the improvements are validated by the objective, standardized rating scores on the Expresssive and Receptive rating scales, both tests for which practice effects are not of concern to reliability.

Not a single child had to discontinue the study due to side effects. Parents reported only sporadic hyperactivity which was alleviated by decreasing the dose. After study completion, we found that particular adjustments of concurrent medications, such as SSRIs or acetylcholinesterase inhibitors, typically resolved the over-active behavior. Previous studies involving carnosine have indicated a very low toxicity level; among 691 cases of adult clinical trials, no symptomatic side effects were reported. Matsukura, T., and Tanaka, H. *Biochemistry (Mosc)* 2000; 65:817-823.

A majority of these children with ASD were those that had a positive history of abnormal EEG or partial response to valproic acid therapy If indeed carnosine acts to affect GABA bioavailability, it may likely alter the subclinical seizure threshold or GABA function. Carnosine is the first dietary supplement that may alter the neuronal function in children with ASD that has been substantiated by a double-blind controlled study. Further study is needed to investigate the mechanism of carnosine supplementation on brain biochemistry. Childhood epilepsy as well as apraxia, cerebral palsy, Rhett's Syndrome, refractive epilepsy, dyslexia, nonverbal learning disabilities, tics, Tourette's, ADD/ADHD, and other conditions may all benefit from the response potentials measured in this study with ASD patients.

Example 5

Carnosine and ADD/ADHD

The purpose of this example is to demonstrate the benefits of treating attention deficit or attention deficit hyperactivity disorder (ADD/ADHD) using carnosine. Patients, having been diagnosed with ADD/ADHD using DSMIVR criteria, are divided into two groups. One group is given a placebo, and the other is given carnosine (e.g., a composition comprising carnosine, zinc and vitamin E). Both placebo and active substance are identical in encapsulated or powdered appearance, without taste or smell. All pills are contained by a gelatin capsule, and when powder is used, patients or parents of patients are instructed to mix the powder with either food or drink. Dosage of carnosine will be 400 mg by mouth, twice a day.

The experiment will last twelve weeks, and every four weeks, the patients will be examined based on the following criteria: common rating scale, parental diary, teaching reports, etc. Statistical analysis will be conducted on the resulting data using a SSPS program, ANOVA f-tests or student t-tests.

Improvements are evaluated for statistical significance. Significant improvement over any parameter used to assess treatment for ADD/ADHD provides an indication that the carnosine composition is a beneficial therapy (or adjuct therapy for subjects on medication during the study). Improvements seen in subjects that are receiving ADD/ADHD medications during the study provide an indication to formulate such medications with carnosine and/or to package unit doses for patients that include their medication in combination with carnosine.

Example 6

Carnosine and Apraxias

The purpose of this example is to demonstrate the benefits of treating apraxias with carnosine. The study is conducted in a manner substantially identical to that described in example 5, except that the patients will have been diagnosed with an apraxia and the patients will be evaluated using criteria relevant to the particular apraxia.

Example 7

Carnosine and Tourette's Syndrome

The purpose of this example is to demonstrate the benefits of treating Tourette's Syndrome with carnosine. The study is conducted in a manner substantially identical to that described in example 5, except that the patients will have been diagnosed with Tourette's and the patients will be evaluated using criteria relevant to Tourette's. Diagnosis is based on clinical history and criteria meeting DSMIVR standards. A tic severity scale such as the Yale Tic Inventory Scale is used. Achenbach and Aberrant Behavorial Checklist is performed. Carnosine is added and evaluated for effect on mood, attention, and tic frequency. Dosage of 400 mg b.i.d. for children under 10 years of age, 800 mg b.i.d. for children 10-16 years of age is used.

Example 8

Carnosine and Dyslexia

The purpose of this example is to demonstrate the benefits of treating dyslexia with carnosine. The study is conducted in a manner substantially identical to that described in example 5, except that the patients will have been diagnosed with dyslexia and the patients will be evaluated using criteria relevant to dyslexia. Patients diagnosed using standard psychometric testing and by meeting clinical criteria for dyslexia are included in the study. A twelve week treatment of 400 mg twice daily. After the twelve weeks patients are reevaluated by testing reading scores or psychometric testing.

Example 9

Carnosine and Mild Depression

The purpose of this example is to demonstrate the benefits of treating mild depression with carnosine. The study is conducted in a manner substantially identical to that described in example 5, except that the patients will have been diagnosed with mild depression and the patients will be evaluated using criteria relevant to mild depression. The dosage for those ages twelve years old and older is 400 mg b.i.d., titrated up to 800 mg b.i.d. Patients are followed for four months with monthly visits to assess progress. DSMIVR criteria, Aberrant Behavior Checklist, and an appropriate depression inventory scale can all be used to assess progress.

Example 10

Carnosine and Mild Depression

Patients diagnosed with a central auditory processing disorder, using audiological evaluation using the Dichotic Rhyme Test, the Completing Sentence Test, Dichotic Digits, Low-Pass Filtered Speech Test, and Frequency (Pitch) Patterns, are given 400 mg b.i.d. of carnosine or a placebo. After twelve weeks patients are retested and the progress of the two groups is compared.

Example 11

Variations on Carnosine Treatment Examples

Examples 1 through 10 describe studies designed to study carnosine's beneficial ability to treat various neurological disorders. Variations of these studies that are also contemplated include using a carnosine analog in addition to or substitution of carnosine itself. For example, one of the various Formula I compounds besides carnosine is employed Example 12

Use of Carnosine to Improve the Efficacy of Anticonvulsant Medication

This example's purpose is to exhibit the beneficial effect of carnosine or other Formula I compound to increase the efficacy of an anticovulsant (AED). The study population is paired to match patients undergoing similar pharmaceutical therapy for the neurological condition under study. In half of the patients (control), medication is supplemented with placebo. In the test population, medications are supplemented with varying dosages of carnosine (e.g., 400 mg, 800 mg, or 1000 mg delivered orally, twice daily) or other compounds described herein. A composition containing carnosine, e.g. carnosine with vitamin E and zinc.

By way of example, child epilepsy patients are pair-matched by the single or combination anticonvulsant therapies they are receiving. If population study permits, the matching is further refined by other parameters such as age, sex, and/or similarity of clinical symptoms of epilepsy, as well as by seizure type (i.e., one study will be of generalized epilepsy, one of myoclonic epilepsy, and one of partial complex seizures. One member of each pair continues to receive their current anticonvulsant therapy plus placebo, and the other member of the pair receive their current therapy in combination with the carnosine compound.

After 8, 10, 12, or 16 weeks, patients are reevaluated with EEG and other tests for cognition, behavior, and language function. Diaries of seizure frequency will be evaluated. Improvements are evaluated for statistical significance. Significant improvement over any parameter provides an indication that the carnosine or other compound is a beneficial adjunct for the particular pharmaceutical therapy being studied. Such improvements provide an indication to formulate the anticonvulant medications with carnosine and/or to package unit doses for patients that include their anticonvulsant medication in combination with carnosine.

In another variation, matched patients are evaluated to determine if combination therapy with their anticonvulsant medication and carnosine (or other compounds described herein) permits reduction in their dosage of anticonvulsant medication without detrimental clinical effect. The ability of carnosine or other compounds to permit medicine dosage reductions is scored as increasing efficacy and is highly beneficial, since many neurological medications are more expensive and have greater side-effects than carnosine.

Example 13

Use of Carnosine to Improve the Efficacy of Selective Serotonin Reuptake Inhibitor Medication This example's purpose is to exhibit the beneficial effect of carnosine or other Formula I compound to increase the efficacy of a selective serotonin reuptake inhibitor. The study is performed with patients diagnosed with depression, and randomized to carnosine and selective serotonin reuptake inhibitor medication together, and selective serotonin reuptake inhibitor medication alone. After six and twelve weeks of treatment, methods appropriate for assessing the effectiveness of selective serotonin reuptake inhibitor medication are employed. Specifically, the severity of depression in the two groups will be compared.

Example 14

Use of Carnosine to Improve the Efficacy of Acetylcholinesterase Medication in Alzheimer's Patients The acetylcholinesterase inhibitor, donepezil hydrochloride (Aricept), has been approved for the treatment of Alzheimer's Disease. This example's purpose is to exhibit the beneficial effect of carnosine or other Formula I compounds to increase the efficacy of an acetylcholinesterase inhibitor in the treatment of Alzheimer's Disease. The study is performed in patients with Alzheimer's Disease requiring an acetylcholinesterase inhibitor. One group of patients is given both carnosine and an acetylcholinesterase inhibitor. Another group of patients is given an acetylcholinesterase inhibitor alone. Tests appropriate for assessing the cognitive state of Alzheimer's Disease patients are used to track the progress of the patients, and to compare the progress of the two groups.

Example 15

Double-blind Trial of Donepezil Hydrochloride in Children with Autistic Spectrum Disorders The following study was performed to demonstrate the efficacy of donepezil hydrochloride (Aricept), an acetylcholinestease inhibitor, in the treatment of children with Autistic spectrum disorders, and could be repeated using other acetylcholinesterase inhibitors as well. The study can similarly be repeated in individuals with Down's Syndrome.

Methods

Participants: Forty-three patients (35 male, 8 female, mean age=6.8 yrs. (SD=1.9 yrs, range 2.1-10.3 yrs) enrolled in a six week double-blind parallel group design with an open label extension. Patients were randomized to receive either (1)

twelve weeks of DH or (2) six weeks of placebo followed by six weeks of DH. Children were asked to participate in consecutive order of entry into the office for regularly scheduled office visit. Inclusion criteria were: males or females, ages 2-10 with prior diagnoses of Autistic Disorder (N=13) or Pervasive Developmental Disorder-Not Otherwise Specified (N=27) as outlined by clinical criteria in the DSM-IV. American Psychiatric Association. *Diagnostic and Statistical Manual of Mental Disorders* (4th ed.). Washington, D.C.: Author 1994. Diagnosis was confirmed by a pediatric neurologist after completing a comprehensive neurological evaluation and also by a clinical interview with a clinical psychologist. No child was excluded based upon intelligence estimate or developmental language level. Children were not eligible for participation if they had a concomitant neurological syndrome or disease in which neurological compromise is a feature (e.g., neurofibromatosis).

We included patients with abnormal electroencephalograns (EEGs) as they represent an important section of the ASD population. Hollander, E. et al., *J. Clin. Psychiatry* 2001; 62(7): 530-534. Twenty-eight participants (72%) had been previously diagnosed with nocturnal epileptiform EEG abnormalities, while II children (28%) had normal 24-hour EEG patterns. Four had never had an EEG. Patients were maintained on the medications that they had initiated prior to study start: anticonvulsants (N=32, divalproex sodium, valproic acid or lamotrigine), the leading treatment for ASD epileptiform abnormalities. Hollander, E. et al., *J. Clin. Psychiatry* 2001; 62(7): 530-534 DiMartino, A. and Tuchman, R. F., *Pediatric Neurology* 2001; 25(3): 199-207. Other patients were maintained on corticosteroids (N=6, pulse-dose prednisone or prednisolone), CNS stimulants (N=8, dextroamphetamine/amphetamine or methylphenidate), antidepressants (N=7, fluoxetine hydrochloride or paroxetine), antipsychotics (N=4, risperidone), or alpha adrenergic blocking agents (N=9, clonidine).

Participation in the study was voluntary and no compensation for participation was given. The study coordinators obtained written informed consent approved by the Lake Forest Hospital Institutional Review Board from one parent at the baseline visit.

Procedures: At the baseline visit, patients were randomized into two groups, group one receiving 2.5 milligrams of DH and group two receiving placebo. The standard donepezil dosage recommendation of 5 milligrams was halved in accordance with pediatric protocols to arrive at a quantity of 2.5 milligrams. The duration of the double-blind, parallel trial was six weeks, at which time all subjects entered open-label treatment for an additional six weeks.

Medication: Placebo and DH were identical in appearance in capsule (sprinkle) form to allow for easy oral administration. The dose was lowered to 1.25 milligrams or discontinued throughout the 12-week trial if adverse events persisted for more than one week (e.g., irritability, hyperactivity, or gastrointestinal problems). The maximum daily dose was 2.5 milligrams. The medication was adjusted by halving the dose (1.25 mg) if parents noted their children to have tolerable yet persistent gastrointestinal distress, hyperactivity, or irritability. Medication was discontinued if GI intolerability or changes in behavior were considered to be an adverse event (i.e., persisted for more than one day). Medication was administered at dinnertime, unless restlessness occurred in sleep, in which case administration was changed to an earlier time in the day. Dinnertime was selected as the preferred administration time in an attempt to alleviate gastrointestinal side effects observed in the dementia population.

Patient progress and side effects were monitored at the scheduled appointments by study coordinators, nursing staff, and the principal investigator. Weekly telephone contact with parents was documented in telephone logs. The most notable side effects reported in parental diaries and phone conversations were irritability, troubled sleep patterns, and gastrointestinal symptoms of nausea, decreased appetite, or diarrhea.

Parents were not informed whether their child was on placebo or DH until the conclusion of the study. All staff, including nurses, were blinded to the status of the patients on either placebo or drug during the six-week double-blind phase. Patient progress and side effects were monitored at the scheduled appointments by study coordinators, nursing staff, and the primary investigator. Gardner's Receptive One-Word Picture Vocabulary Test (ROWPVT), the EOWPVT-R, and the Childhood Autism Rating Scale (CARS) were administered at baseline, 6-week, and 12-week follow-up visits by the same study coordinator (R.T.):

Outcome Measures: The Receptive One-Word Picture Vocabulary Test, Gardner, M. F. Receptive One-Word Picture Vocabulary Test: ROWPVT. Novato, Calif.: Academic Therapy Publications 1985, examines a child's understanding of language and is an effective tool for assessing receptive language in children with expressive language difficulties. The test was developed for children ages two through twelve. Participants are shown a group of four pictures and asked to point to the picture corresponding to the word presented aurally by the clinician. The test is completed when the child makes six errors of eight consecutive items.

The Expressive One-Word Picture Vocabulary Test—Revised can be used as a tool to determine auditory-visual-verbal association ability as well as expressive language functioning in young children ages two through 12. Gardner, M. F. Expressive One-Word Picture Vocabulary Test (Revised): EOWPVT-R. Novato, Calif.: Academic Therapy Publications 1990. The test was developed to address general concrete concepts, grouping, abstract concepts, and descriptive concepts. Participants are shown a black-and-white picture and asked to identify it verbally. The test is completed when the child makes six consecutive errors.

The Childhood Autism Rating Scale was used to assess changes in autistic features. Schopler, E., Reichler, R. J., Renner, B. R. The Childhood Autism Rating Scale: CARS. Los Angeles, Calif.: Western Psychological Sciences 1988. It was designed as a rating system for identification of behavioral symptoms and for classification purposes by replacing subjective clinical judgments with objective and quantifiable ratings based upon direct behavioral observation. We adapted the interview-based clinician assessment to a parental rating report that was completed together with the research coordinator at the time of the 6 and 12-week clinic appointments. We asked that the same parent complete the CARS scale each time for the sake of consistency and homogeneity in assessment. The study coordinators asked the parent to form an impression of the child from the last six weeks when completing the CARS at each visit. The CARS is divided into 15 subcategories, each scored by increments of 0.5 points on a scale of one through four, which are cumulatively added resulting in a total score ranging from 15 to 60. The rating scale for total scores is then divided into three classifications: Non-autistic (15-30), Mildly/Moderately Autistic (30.5-36), and Severely Autistic (36.5-60). A lower total score, therefore, designates a less severe rating.

Data were analyzed using the SPSS Statistical Package, Version 10.0. Independent samples t-tests were conducted for the planned contrasts between Group I and Group II. Paired samples t-tests were conducted for analyses of change in CARS, EOWPVT-R, and ROWPVT scores within groups.

Results

Group I and Group II were statistically equivalent at baseline (See Table 1.), all $p<0.05$.

TABLE 1

Characteristics of study subjects.

| BASELINE | Group I (N = 23) (DH, DH) | Group II (N = 20) Placebo, DH) |
|---|---|---|
| Age (yrs.) | 6.8 (range 2.1-9.9) | 6.8 (range 4.1-10.3) |
| CARS | 34.7 (range 20.5-48.5) | 35.1 (range 19.5-47.5) |
| Exp. Speech Age (mos.) | 35.7 (range 0-74.0) | 31.9 (range 0-113.0) |
| Rec. Speech Age (mos.) | 38.8 (range 0-71.0) | 33.5 (range 0-98.0) |

Both groups were statistically equivalent at BASELINE for all variables.

Descriptive statistics for Group I CARS, EOWPVT-R, and ROWPVT baseline to six-week and twelve-week follow-up are provided in Table 2. Improvements in speech and language were apparent at 6 weeks, and improvements were stable through week 12 when compared to baseline. Improvements in CARS scores are indicated by lowered scores, which were most pronounced by week 12.

A change of three points or more in either direction was considered to be clinically meaningful as it could allow a child to change categorical class, given a baseline average of 34.7. In Group I, 50% of children had CARS change scores ([Baseline]–[6 Week score]) indicating improvement of 3.0 or greater; Group II showed that 30% of CARS scores improved 3 points or greater. Clinically meaningful worsening of CARS scores from Baseline to Week 6 were apparent in 12.5% of Group I, and 30% of Group II. Item analysis for the CARS did not reveal any specific items within the CARS total score that "carried" the changes in overall scores. With adjustment for multiple comparisons, and to take into consideration the potential for maturation and "learning" with test-retest, we adjusted our significance levels with a Tukey's test for multiple comparisons.

TABLE 2

Changes in behavior and language measures for Group I (DH, DH).

| | BASELINE | 6-WEEK | 12-WEEK |
|---|---|---|---|
| CARS | 34.7 (SD = 7.7) | 33.3 (SD = 8.0) | 30.8 (SD = 7.9)** |
| Exp. Speech Age (mos.) | 35.7 (SD = 27.8) | 43.3 (SD = 27.2)* | 42.5 (SD = 28.5)*** |

TABLE 2-continued

Changes in behavior and language measures for Group I (DH, DH).

| | BASELINE | 6-WEEK | 12-WEEK |
|---|---|---|---|
| Rec. Speech Age (mos.) | 38.8 (SD = 23.5) | 50.3 (SD = 27.0)* | 49.7 (SD = 34.2)*** |

*$p < .05$, BL compared to 6 week
**$p < .05$, BL compared to 12 week
***$p < .05$, BL compared to 6 and 12 week Table 3 shows the changes in speech and behavior for children administered placebo for the first six weeks, followed by six weeks of DH.

TABLE 3

Changes in speech and autistic behaviors for children in Group II (Placebo, DH).

| | BASELINE → placebo | 6-WEEK | 12-WEEK |
|---|---|---|---|
| CARS | 35.1 (SD = 7.9) | 32.9 (SD = 7.7)* | 30.9 (SD = 9.1)* |
| Exp. Speech Age (mos.) | 31.9 (SD = 31.1) | 33.8 (SD = 32.9) | 40.9 (SD = 38.8)***@ |
| Rec. Speech Age (mos.) | 33.5 (SD = 27.9) | 39.83 (SD = 27) | 87.37 (SD = 14.2)**@ |

*$p < .05$, BL compared to 12 week or BL compared to 6 week
**$p < .05$, 6 compared to 12 week
***$p < .05$, BL compared to both 6 and 12 week
@reduced N (=16) weeks 6 → 12, subjects lost to follow-up Table 4 shows the results of combining the six week treatment data for the two groups. The results of the first six weeks from Group I were combined with the six weeks of treatment for Group II. It is important to note that this combined group therefore contains the data from subjects who were both blinded (Group 1) and unblinded (Group 2) to control for any expectancy effects. Statistically significant changes were observed across all three domains.

TABLE 4

Combination of Group I with Group II subjects treated with DH for six weeks.

| | BASELINE | 6-weeks DH | p value |
|---|---|---|---|
| CARS (N = 35) | 34.7 (SD = 7.4) | 32.2 (SD = 8.5) | .004 |
| Exp. Speech Age (N = 31) | 39.3 (SD = 27.9) | 43.6 (SD = 31.8) | .044 |
| Rec. Speech Age (N = 31) | 43.7 (SD = 22.2) | 53.2 (SD = 25.8) | .002 |

Side Effects: Nine patients dropped from the study after the first 6 weeks: 6/9 of these had been on DH when the code was broken. These patients discontinued due to reports of diarrhea or stomach cramping in 2 patients. Increased irritability, accompanied by increased screaming and vocalizations were the most common behavioral complaints in the other 4 patients.

Discussion

The results of this trial of DH in pediatric autistic spectrum patients suggest that receptive language, expressive language, and overall general autistic features can improve with pharmacological stimulation of acetylcholinergic receptors. Although we cannot conclude that the results were due solely to the addition of DH, several factors lend support to our conclusion that its effect was valid. All children had their medications held constant, and no changes to the childrens' environments were undertaken during the study duration (e.g., no new behavioral interventions). Second, the effect of time alone indicates that children with ASD do not follow a typical course of language maturation, since improvement in speech and language, as well as severity of autistic behaviors, did not change significantly for children on placebo.

After as little as six weeks on an acetylcholinesterase inhibitor, changes in expressive and receptive speech were: 1.) apparent by parental report, 2.) measurable via standardized rating instruments, and 3.) statistically significant. There were reports of increases in spontaneous nonprompted behaviors that accompanied increases in verbalizations and vocalizations, consistent with hypothetical cortical arousal of the frontal cortex and cholinergic innervations.

The statistical significance of changes in our measurements of vocabulary and CARS behavior were further supported by parental reports of verbal expressions that appeared to become more laden with emotional content, differing in quantity from simple requests to commands. Improvements in speech quality, such as increased fluency and improved dysarthria, were also observed when compared to the often staccato-like and non-rhythmic speech prior to treatment. Stimulation of Broca's area has been shown to affect speech in a similar manner to what was observed in this population. Ojemann, G. A., et al., *Localization and Physiological Correlates of Language and Verbal Memory in Human Lateral Temporoparietal Cortex*. In A. B. Scheibel & A. F. Wechsler (Eds.) *Neurobiology of Higher Cognitive Function*. New York: Guilford Press 1990. Greater ease in nonverbal imitation was frequently reported, perhaps reflecting decreased apraxia along with more fluid and less rigid behavioral repertoires.

Although the use of DH in pediatric autistic or pervasive developmental disorder patients has not previously been described, the side effects observed were limited to those reported in prior studies of adult populations. Green, Y. M. et al., *J. Clin. Psychiatry* 1999; 60: 56-57. Rogers, S. L. et al., *Dementia* 1996; 7: 293-303. Wengel, S. P. et al., *Am. J. Psychiatry* 1998; 155 (11): 1632-1633. The side effect profile of DH use in children confirms that it is well tolerated with irritability, hyperactivity, and mild gastrointestinal upset seen in a small subset of participants. Decreasing the daily dosage from 2.5 to 1.25 milligrams often ameliorated persistent side effects, with very few patients dropping out. The most common adverse event was the concomitant increase in mood swings and lability, which could be consistent with a pseudobulbar phenomenon. Reports of increases in lability, crying, and irritability were often accompanied by reports of increased exploration of environment and increased affection, for example. In many cases, parents viewed these negative temperaments as an "awakening" of the previously aloof affect of their child. Clinically meaningful reports of improvements in expressive and receptive speech can be adequately tracked and measured in this population. Clinical observations supported alterations in exploratory behaviors consistent with those we hypothesized would be affected by DH.

Although no data has previously been reported about long-term use of DH in this or any other large pediatric population, subsequent observation of our clinical population has suggested long term effectiveness, toleration of side effects, and even increased dosage titration in many of our patients. We have subsequently followed over 100 children with ASD on DH for up to 20 months since the conclusion of this study. No obvious long-term deficits or suspected down-regulation effect was seen. In addition, when patients stopped the medication after 6 additional months, no patients had major regressions or lost skills that had previously been gained. Further long-term use of cholinesterase inhibitors may lead to greater understanding of the possible ability to sustain new neuronal connections in a brain that has more neuronal plasticity than the elderly with Alzheimer's Disease.

Continuing study should focus on the behavioral features of ASD that were reported by parents via a more systematic assessment (such as the Autism Diagnostic Observation Scale) to quantify change. The quest for a reliable, standardized, normalized rating instrument to assess clinical efficacy in clinical drug trials in the field of autism remains a current subject of inquiry. Roseman, B. et al., *J. Autism and Develop. Disorders* 2001; 31 (3): 361-362. Small sample size precluded assessment of subgroups of children on varying medication combinations, or analysis of EEG correlates. Further research will help to determine if certain children appreciated more language gains in relationship to drug regimens (i.e., drug-drug interactions). Despite these caveats, DH was observed to improve speech above "placebo effect" reported in other ASD drug trials, King, B. H. et al., *J. Am. Acad. Child and Adolescent Psychiatry* 2001; 40 (6): 658-665, in both receptive and expressive domains while still having a benign safety profile in this pediatric sample.

Example 16

Use of Carnosine to Improve the Efficacy of Acetylcholinesterase Medication in Autism Spectral Disorder Patients This example's purpose is to exhibit the beneficial effect of carnosine or other Formula I compound to increase the efficacy of an acetylcholinesterase inhibitor in patients with Autistic spectrum disorders. One group of patients is given both carnosine and an acetylcholinesterase inhibitor. Another group of patients is given an acetylcholinesterase inhibitor alone. Tests appropriate for assessing the cognitive function of Autistic spectrum disorder children are used to track the progress of the patients, and to compare the progress of the two groups, as described in detail in Example 15. The study can similarly be repeated in individuals with Tourette's Syndrome, ADD/ADHD and Down's Syndrome with appropriate modifications in testing when necessary.

Example 17

Use of Carnosine to Improve the Efficacy of ADD/ADHD Medication

This example's purpose is to exhibit the beneficial effect of carnosine or other Formula I compound to increase the efficacy of an ADD/ADHD medication. The study is performed in a manner substantially identical to that described in example 12, with the substitution of ADD/ADHD medication in place of anticonvulsant medication, and the use of tests appropriate for assessing the effectiveness of ADD/ADHD medication. Specifically, common rating scales, teacher reports and parental diaries are employed.

Example 18

Use of Carnosine to Improve the Efficacy of Pervasive Developmental Disorder Medication This example's purpose is to exhibit the beneficial effect of carnosine or other Formula I compound to increase the efficacy of a pervasive developmental disorder medication. The study is performed in a manner substantially identical to that described in example 12, with the substitution of medications if necessary, and the use of parameters appropriate for assessing the effectiveness of pervasive developmental disorder medication.

Example 19

Use of Carnosine to Improve the Efficacy of Stimulant Medication

This example's purpose is to exhibit the beneficial effect of carnosine or other Formula I compound to increase the efficacy of a stimulant. The study is performed in a manner substantially identical to that described in example 12, with the substitution of stimulant medication in place of anticonvulsant medication, and the use of parameters appropriate for assessing the effectiveness of stimulant medication.

Example 20

Variation on Drug Efficacy Improvement Examples

Examples 12 through 19 describe studies designed to study carnosine's beneficial ability to increase the efficacy of various types of medications. Variations of these studies that are also contemplated include using a carnosine analog in addition or substitution of carnosine itself. For example, one of the various Formula I compounds besides carnosine is employed.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method of improving neurological function in a human subject comprising:
    identifying a human subject diagnosed with autism and
    administering to the human subject a composition comprising at least one compound having a structural formula:

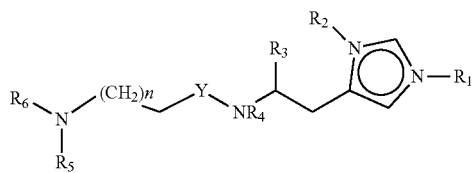

wherein Y is C=O (carbonyl), or SO$_2$, (sulphonyl);
R$_1$ is H or CH$_3$ (methyl), with the proviso that R$_1$ is null when R$_2$ is substituted;
R$_2$ is H or CH$_3$, with the proviso that R$_2$ is null when R$_1$ is substituted;
R$_3$ is COOH (carboxyl) or H;
R$_4$ is H;
R$_5$ is H or COCH$_3$, with the proviso that R$_5$ is H when R$_6$ is COCH$_3$;
R$_6$ is H or COCH$_3$, with the proviso that R$_6$ is H when R$_5$ is COCH$_3$; and n is 1 or 2;
or a pharmaceutically acceptable salt, hydrate, or prodrug thereof; and
binding the at least one compound to neurotransmitter gamma-aminobutyric acid.

2. The method according to claim 1, wherein the composition further comprises a pharmaceutically acceptable diluent, adjuvant, excipient, or carrier.

3. The method according to claim 1, wherein the composition comprises at least one compound selected from the group consisting of carnosine, homocarnosine, anserine, ophidine, carcinine, N-acetyl-carnosine, N-acetyl-homocarnosine, N-acetyl-anserine, N-acetyl-ophidine, and N-acetyl-carnicine.

4. The method according to claim 1, wherein the composition comprises carnosine.

5. The method of claim 1, wherein the composition comprises carnosine; an ion of a metal selected from the group consisting of zinc, copper and iron; and a vitamin selected from the group consisting of vitamin B$_6$ and vitamin E.

6. A method of improving neurological function in a human subject comprising:
    identifying a human subject diagnosed with autism;
    administering to the human subject a composition comprising a neuromodulator selected from the group consisting of anticonvulsant medication, selective serotonin reuptake inhibitor medication, acetylcholinesterase medication, pervasive developmental disorder medication, attention deficit disorder/attention deficit hyperactive disorder (ADD/ADHD) medication, and stimulant medication in admixture with a compound of the formula:

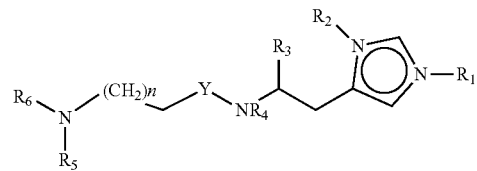

wherein Y is C=O carbonyl), or SO$_2$, (sulphonyl);
R$_1$ is H or CH$_3$ (methyl), with the proviso that R$_1$ is null when R$_2$ is substituted;
R$_2$ is H or CH$_3$, with the proviso that R$_2$ is null when R$_1$ is substituted;
R$_3$ is COOH (carboxyl) or H;
R$_4$ is H;
R$_5$ is H or COCH$_3$, with the proviso that R$_5$ is H when R$_6$ is COCH$_3$;
R$_6$ is H or COCH$_3$, with the proviso that R$_6$ is H when R$_5$ is COCH$_3$; and
n is 1 or 2;
or a pharmaceutically acceptable salt, hydrate, or prodrug thereof; and
binding the composition to neurotransmitter gamma-aminobutyric acid.

7. A method of improving neurological function in a human subject comprising:
    identifying a human subject diagnosed with autism;
    administering to the human subject a unit dose comprising:
    a first compound selected, selected from the group consisting of anticonvulsant medication, selective serotonin reuptake inhibitor medication, acetylcholinesterase medication, pervasive developmental disorder medication, attention deficit disorder/attention deficit hyperactive disorder (ADD/ADHD) medication, and stimulant medication; and a second compound of the formula:

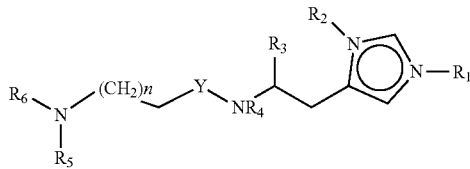

wherein Y is C=O (carbonyl), or $SO_2$, (sulphonyl);
$R_1$ is H or $CH_3$ (methyl), with the proviso that $R_1$ is null when $R_2$ is substituted;
$R_2$ is H or $CH_3$, with the proviso that $R_2$ is null when $R_1$ is substituted;
$R_3$ is COOH (carboxyl) or H;
$R_4$ is H;
$R_5$ is H or $COCH_3$, with the proviso that $R_5$ is H when $R_6$ is $COCH_3$;
$R_6$ is H or $COCH_3$, with the proviso that $R_6$ is H when $R_5$ is $COCH_3$; and
n is 1 or 2;
or a pharmaceutically acceptable salt, hydrate, or prodrug thereof;
wherein the first and second compounds are packaged together for co-administration to a human subject, but are not in admixture; and
binding the second compound to neurotransmitter gamma-aminobutyric acid.

8. The method according to claim 1, comprising administering to the human subject 100-5000 mg of the composition.

9. The method according to claim 6, comprising administering to the human subject 100-5000 mg of the composition.

10. The method according to claim 7, comprising administering to the human subject 100-5000 mg of the composition.

* * * * *